(12) United States Patent
Grether et al.

(10) Patent No.: US 9,512,132 B2
(45) Date of Patent: Dec. 6, 2016

(54) PYRAZOLE COMPOUNDS AS CB2 AGONISTS

(71) Applicant: Hoffmann-La Roche Inc., Little Falls, NJ (US)

(72) Inventors: Uwe Grether, Efringen-Kirchen (DE); Atsushi Kimbara, Shizuoka (JP); Nettekoven Matthias, Grenzach-Wyhlen (DE); Ricklin Fabienne, Hombourg (FR); Roever Stephan, Inzlingen (DE); Mark Rogers-Evans, Bottmingen (CH); Tanja Schulz-Gasch, Ziefen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/844,991

(22) Filed: Sep. 3, 2015

(65) Prior Publication Data
US 2015/0376192 A1    Dec. 31, 2015

Related U.S. Application Data

(63) Continuation of application No. PCT/EP2014/054107, filed on Mar. 4, 2014.

(30) Foreign Application Priority Data

Mar. 7, 2013    (EP) .................................... 13158233

(51) Int. Cl.
| | | |
|---|---|---|
| *A61K 31/437* | (2006.01) | |
| *A61K 31/519* | (2006.01) | |
| *C07D 471/04* | (2006.01) | |
| *C07D 487/04* | (2006.01) | |
| *C07D 473/04* | (2006.01) | |

(52) U.S. Cl.
CPC ........... *C07D 487/04* (2013.01); *C07D 471/04* (2013.01); *C07D 473/04* (2013.01)

(58) Field of Classification Search
CPC ........................... C07D 471/04; C07D 487/04
See application file for complete search history.

(56) References Cited

U.S. PATENT DOCUMENTS

2012/0316147 A1    12/2012    Bissantz

FOREIGN PATENT DOCUMENTS

| WO | 01/58869 A2 | 8/2001 |
|---|---|---|
| WO | 03/082191 A2 | 10/2003 |
| WO | 03/093269 A2 | 11/2003 |
| WO | 2006/047516 A2 | 5/2006 |
| WO | 2009/051705 A1 | 4/2009 |
| WO | 2010/118367 A2 | 10/2010 |
| WO | 2013/068306 A1 | 5/2013 |
| WO | 2014/005968 A1 | 1/2014 |
| WO | 2014/086705 A1 | 6/2014 |
| WO | 2014/086805 A1 | 6/2014 |
| WO | 2014/086806 A1 | 6/2014 |
| WO | 2014/086807 | 6/2014 |

OTHER PUBLICATIONS

Cheng et al., "Potential Purine Antagonists. VII. Synthesis of 6-Alkylpyrazolo[3,4-d]pyrimidines" Journal of Organic Chemistry 23:191-200 ( 1958).

Cheng et al., "Potential Purine Antagonists. XII. Synthesis of 1-Alkyl(aryl)-4,6-disubstituted Pyra~olo(3,4-d]pyrimidines" Journal of Organic Chemistry 23:852-861 ( 1958).

ISR for WO2014/135507, PCT/EP2014/054107.

Nettekoven et al., "Highly potent and selective cannabinoid receptor 2 agonists: initial hit optimization of an adamantyl hit series identified from high-through-put screening" Bioorg Med Chem Lett. 23(5):1177-81 ( 2013).

Senga et al., "Synthesis and Xanthine Oxidase Inhibitory Activity of 4,6-Disubstituted 1-p-Chlorophenylpyrazolo[3,4-d]pyrimidines" Journal of Hererocyclic Chemistry 19(6):1565-67 ( 1982).

Slavik et al., "Discovery of a high affinity and selective pyridine analog as a potential positron emission tomography imaging agent for cannabinoid type 2 receptor" J Med Chem. 58(10):4266-77 ( 2015).

*Primary Examiner* — Brian McDowell
(74) *Attorney, Agent, or Firm* — Alex Andrus

(57) ABSTRACT

The invention relates to a compound of formula (I)

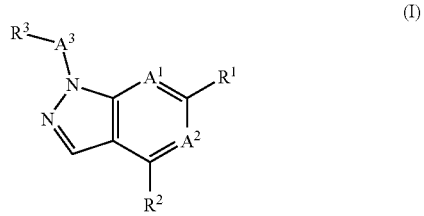

wherein $A^1$ to $A^3$ and $R^1$ to $R^3$ are defined as in the description and in the claims. The compound of formula (I) can be used as a medicament.

16 Claims, No Drawings

PYRAZOLE COMPOUNDS AS CB2 AGONISTS

CROSS-REFERENCE TO RELATED APPLICATIONS

This application is a continuation application of International Application No. PCT/EP2014/054107, filed on Mar. 4, 2014, which claims priority to European Patent Application No. 13158233.0, filed on Mar. 7, 2013, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

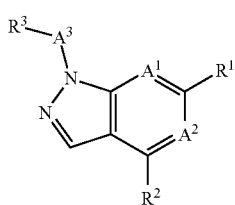

wherein $A^1$ is carbon or nitrogen;
$A^2$ is carbon or nitrogen;
$A^3$ is —$(CH_2)_n$— or —$CH_2C(O)$—;
$R^1$ is alkyl, cycloalkyl, alkoxy or halogen;
$R^2$ is alkoxy, substituted pyrrolidinyl or substituted dihydropyrrolyl, wherein substituted pyrrolidinyl and substituted dihydropyrrolyl are pyrrolidinyl and dihydropyrrolyl substituted with one or two substituents independently selected from halogen, hydroxyl, hydroxyalkyl, alkoxyalkyl and alkylfurazanylalkoxy;
$R^3$ is phenyl, substituted phenyl, substituted furazanyl, pyridinyl, substituted pyridinyl, dioxothietanyl, tetrahydrofuranyl, substituted tetrazolyl or substituted triazolyl, wherein substituted phenyl, substituted furazanyl, substituted pyridinyl and substituted triazolyl are phenyl, pyridinyl and triazolyl substituted with one or two substituents independently selected from alkyl, alkoxy, halogen, haloalkyl, alkylsulfonyl and cycloalkyl, and wherein substituted tetrazolyl and substituted furazanyl are tetrazolyl and furazanyl substituted with one substituent selected from alkyl, alkoxy, halogen, haloalkyl, alkylsulfonyl and cycloalkyl;
n is 0, 1 or 2;
provided that $A^1$ and $A^2$ are not both carbon at the same time;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the PR injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy, tert.-butoxy and neopentyloxy. Particular "alkoxy" are methoxy, ethoxy and neopentyloxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to three halogens, i.e. one, two or three halogens.

The term "haloalkyl", alone or in combination, denotes an alkyl group substituted with at least one halogen, particularly substituted with one to five halogens, particularly one to three halogens. A particular "haloalkyl" is trifluoromethyl.

The terms "hydroxyl" and "hydroxy", alone or in combination, signify the —OH group.

The term "carbonyl", alone or in combination, signifies the —C(O)— group.

The term "sulfonyl", alone or in combination, signifies the —S(O)$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to:
  A compound of formula (I) wherein $A^1$ is nitrogen;
  A compound of formula (I) wherein $A^2$ is nitrogen;
  A compound of formula (I) wherein $A^3$ is —$(CH_2)_n$—;
  A compound of formula (I) wherein $A^3$ is —$CH_2$—;
  A compound of formula (I) wherein $R^1$ is alkyl or cycloalkyl;
  A compound of formula (I) wherein $R^1$ is alkyl;
  A compound of formula (I) wherein $R^1$ is tert.-butyl or cyclopropyl;
  A compound of formula (I) wherein $R^1$ is tert.-butyl;
  A compound of formula (I) wherein $R^2$ is halopyrrolidinyl, hydroxypyrrolidinyl, alkoxy, halodihydropyrrolyl, alkylfurazanylalkoxy, hydroxyalkylpyrrolidinyl or alkoxyalkylpyrrolidinyl;
  A compound of formula (I) wherein $R^2$ is difluoropyrrolidinyl, hydroxypyrrolidinyl, ethoxy, fluorodihydropyrrolyl, methylfurazanylmethoxy, hydroxymethylpyrrolidinyl or methoxymethylpyrrolidinyl;
  A compound of formula (I) wherein $R^2$ is substituted pyrrolidinyl, wherein substituted pyrrolidinyl is pyrrolidinyl substituted with one or two substituents independently selected from halogen and hydroxyl;
  A compound of formula (I) wherein $R^2$ is difluoropyrrolidinyl or hydroxypyrrolidinyl;
  A compound of formula (I) wherein $R^3$ is phenyl, alkoxyphenyl, halophenyl, haloalkylphenyl, alkylfurazanyl, alkylsulfonylphenyl, pyridinyl, halopyridinyl, dioxothietanyl, tetrahydrofuranyl, alkyltetrazolyl, cycloalkyltetrazolyl, dialkyltriazolyl or alkyltriazolyl;
  A compound of formula (I) wherein $R^3$ is phenyl, methoxyphenyl, chlorophenyl, chlorofluorophenyl, trifluoromethylphenyl, methylfurazanyl, methylsulfonylphenyl, pyridinyl, chloropyridinyl, dioxothietanyl, tetrahydrofuranyl, methyltetrazolyl, cyclopropyltetrazolyl, dimethyltriazolyl or methyltriazolyl;
  A compound of formula (I) wherein $R^3$ is substituted phenyl, substituted furazanyl, substituted pyridinyl, substituted tetrazolyl or substituted triazolyl, wherein substituted phenyl, substituted pyridinyl and substituted triazolyl are phenyl, pyridinyl and triazolyl substituted with one or two substituents independently selected from alkyl, halogen and haloalkyl, wherein substituted tetrazolyl is tetrazolyl substituted with one substituent selected from alkyl, and cycloalkyl, and wherein substituted furazanyl is furazanyl substituted with alkyl;
  A compound of formula (I) wherein $R^3$ is trifluoromethylphenyl, methylfurazanyl, chloropyridinyl, methyltetrazolyl, cyclopropyltetrazolyl, dimethyltriazolyl or methyltriazolyl; and
  A compound of formula (I) wherein n is 1.

The invention further relates in particular to a compound of formula (I) selected from
  6-tert-Butyl-4-(3,3-difluoro-pyrrolidin-1-yl)-[(4-methoxyphenyl)methyl]-1H-pyrazolo[3,4-d]pyrimidine;
  1-Benzyl-6-tert-butyl-4-(3,3-difluoro-pyrrolidin-1-yl)-1H-pyrazolo[3,4-d]pyrimidine;
  (S)-1-[6-tert-Butyl-1-[(2-chlorophenyl)methyl]-1H-pyrazolo[3,4-d]pyrimidin-4-yl]-pyrrolidin-3-ol;
  6-tert-Butyl-1-[(2-chlorophenyl)methyl]-4-(3,3-difluoro-pyrrolidin-1-yl)-1H-pyrazolo[3,4-d]pyrimidine;
  6-tert-Butyl-1-[(2-chlorophenyl)methyl]-4-ethoxy-1H-pyrazolo[3,4-d]pyrimidine;
  6-tert-Butyl-1-[(2-chloro-4-fluorophenyl)methyl]-4-(3,3-difluoro-pyrrolidin-1-yl)-1H-pyrazolo[3,4-d]pyrimidine;
  6-tert-Butyl-4-(3,3-difluoro-pyrrolidin-1-yl)-1-[(2-trifluoromethylphenyl)methyl]-1H-pyrazolo[3,4-d]pyrimidine;
  6-tert-Butyl-4-(3,3-difluoro-pyrrolidin-1-yl)-1-phenethyl-1H-pyrazolo[3,4-d]pyrimidine;
  6-tert-Butyl-4-(3,3-difluoro-pyrrolidin-1-yl)-1-(4-methyl-furazan-3-ylmethyl)-1H-pyrazolo[3,4-d]pyrimidine;
  6-tert-Butyl-4-(3,3-difluoro-pyrrolidin-1-yl)-1-(2-methanesulfonyl-benzyl)-1H-pyrazolo[3,4-d]pyrimidine;
  6-tert-Butyl-4-(3,3-difluoro-pyrrolidin-1-yl)-1-(2-pyridin-3-yl-ethyl)-1H-pyrazolo[3,4-d]pyrimidine;
  6-tert-Butyl-1-(2-chloro-pyridin-3-ylmethyl)-4-(3,3-difluoro-pyrrolidin-1-yl)-1H-pyrazolo[3,4-d]pyrimidine;
  6-tert-Butyl-4-(3,3-difluoro-pyrrolidin-1-yl)-1-(1,1-dioxo-1λ6-thietan-3-yl)-1H-pyrazolo[3,4-d]pyrimidine;
  6-tert-Butyl-4-(3,3-difluoro-pyrrolidin-1-yl)-1-(tetrahydro-furan-3-yl)-1H-pyrazolo[3,4-d]pyrimidine;
  6-tert-Butyl-4-(3,3-difluoro-pyrrolidin-1-yl)-1-(1-methyl-1H-tetrazol-5-ylmethyl)-1H-pyrazolo[3,4-d]pyrimidine;
  6-tert-Butyl-1-(1-cyclopropyl-1H-tetrazol-5-ylmethyl)-4-(3,3-difluoro-pyrrolidin-1-yl)-1H-pyrazolo[3,4-d]pyrimidine;
  6-tert-Butyl-4-(3,3-difluoro-pyrrolidin-1-yl)-1-(4,5-dimethyl-4H-[1,2,4]triazol-3-ylmethyl)-1H-pyrazolo[3,4-d]pyrimidine;
  6-tert-Butyl-1-(4,5-dimethyl-4H-[1,2,4]triazol-3-ylmethyl)-4-(3-fluoro-2,5-dihydro-pyrrol-1-yl)-1H-pyrazolo[3,4-d]pyrimidine;
  6-tert-Butyl-4-(3,3-difluoro-pyrrolidin-1-yl)-1-(3-methyl-3H-[1,2,3]triazol-4-ylmethyl)-1H-pyrazolo[3,4-d]pyrimidine;
  6-tert-Butyl-4-(3-fluoro-2,5-dihydro-pyrrol-1-yl)-1-(3-methyl-3H-[1,2,3]triazol-4-ylmethyl)-1H-pyrazolo[3,4-d]pyrimidine;
  2-[6-tert-Butyl-4-(3,3-difluoro-pyrrolidin-1-yl)-pyrazolo[3,4-d]pyrimidin-1-yl]-1-pyridin-4-yl-ethanone;
  2-[6-tert-Butyl-4-(3,3-difluoro-pyrrolidin-1-yl)-pyrazolo[3,4-d]pyrimidin-1-yl]-1-pyridin-2-yl-ethanone;
  (S)-1-[6-tert-Butyl-1-[(4-methoxyphenyl)methyl]-1H-pyrazolo[3,4-d]pyrimidin-4-yl]-pyrrolidin-3-ol;
  6-Cyclopropyl-4-(3,3-difluoro-pyrrolidin-1-yl)-1-[(4-methoxyphenyl)methyl]-1H-pyrazolo[3,4-b]pyridine;
  (S)-1-[6-tert-Butyl-1-(4-methyl-furazan-3-ylmethyl)-1H-pyrazolo[3,4-d]pyrimidin-4-yl]-pyrrolidin-3-ol;
  6-tert-Butyl-4-[(S)-3-(4-methyl-furazan-3-ylmethoxy)-pyrrolidin-1-yl]-1-(4-methyl-furazan-3-ylmethyl)-1H-pyrazolo[3,4-d]pyrimidine;

6-Cyclopropyl-4-(3,3-difluoro-pyrrolidin-1-yl)-1-(4-methyl-furazan-3-ylmethyl)-1H-pyrazolo[4,3-c]pyridine;
6-Cyclopropyl-4-(3,3-difluoro-pyrrolidin-1-yl)-1-(4-methyl-furazan-3-ylmethyl)-1H-pyrazolo[3,4-b]pyridine;
(S)-1-[6-tert-Butyl-1-[(2-trifluoromethylphenyl)methyl]-1H-pyrazolo[3,4-d]pyrimidin-4-yl]-pyrrolidin-3-ol;
(S)-1-[6-tert-Butyl-1-(2-methanesulfonyl-benzyl)-1H-pyrazolo[3,4-d]pyrimidin-4-yl]-pyrrolidin-3-ol;
(S)-1-[6-tert-Butyl-1-(1-methyl-1H-tetrazol-5-ylmethyl)-1H-pyrazolo[3,4-d]pyrimidin-4-yl]-pyrrolidin-3-ol;
(S)-1-[6-tert-Butyl-1-(3-chloro-pyridin-2-ylmethyl)-1H-pyrazolo[3,4-d]pyrimidin-4-yl]-pyrrolidin-3-ol;
(S)-1-[6-tert-Butyl-1-(1-cyclopropyl-1H-tetrazol-5-ylmethyl)-1H-pyrazolo[3,4-d]pyrimidin-4-yl]-pyrrolidin-3-ol;
{(R)-1-[6-tert-Butyl-1-[(2-trifluoromethylphenyl)methyl]-1H-pyrazolo[3,4-d]pyrimidin-4-yl]-pyrrolidin-2-yl}-methanol;
6-tert-Butyl-4-((R)-2-methoxymethyl-pyrrolidin-1-yl)-1-[(2-trifluoromethylphenyl)methyl]-1H-pyrazolo[3,4-d]pyrimidine; and
6-tert-Butyl-4-((R)-2-methoxymethyl-pyrrolidin-1-yl)-1-(4-methyl-furazan-3-ylmethyl)-1H-pyrazolo[3,4-d]pyrimidine.

The invention further relates to a compound of formula (I) selected from
6-Chloro-4-(3,3-difluoropyrrolidin-1-yl)-1-[[2-(trifluoromethyl)phenyl]methyl]pyrazolo[3,4-d]pyrimidine; and
4-(3,3-Difluoropyrrolidin-1-yl)-6-(2,2-dimethyl-propoxy)-1-[[2-(trifluoromethyl)phenyl]methyl]pyrazolo[3,4-d]pyrimidine.

The invention also relates in particular to a compound of formula (I) selected from
6-tert-Butyl-4-(3,3-difluoro-pyrrolidin-1-yl)-1-[(2-trifluoromethylphenyl)methyl]-1H-pyrazolo[3,4-d]pyrimidine;
6-tert-Butyl-4-(3,3-difluoro-pyrrolidin-1-yl)-1-(4-methyl-furazan-3-ylmethyl)-1H-pyrazolo[3,4-d]pyrimidine;
6-tert-Butyl-1-(2-chloro-pyridin-3-ylmethyl)-4-(3,3-difluoro-pyrrolidin-1-yl)-1H-pyrazolo[3,4-d]pyrimidine;
6-tert-Butyl-4-(3,3-difluoro-pyrrolidin-1-yl)-1-(1-methyl-1H-tetrazol-5-ylmethyl)-1H-pyrazolo[3,4-d]pyrimidine;
6-tert-Butyl-1-(1-cyclopropyl-1H-tetrazol-5-ylmethyl)-4-(3,3-difluoro-pyrrolidin-1-yl)-1H-pyrazolo[3,4-d]pyrimidine;
6-tert-Butyl-4-(3,3-difluoro-pyrrolidin-1-yl)-1-(4,5-dimethyl-4H-[1,2,4]triazol-3-ylmethyl)-1H-pyrazolo[3,4-d]pyrimidine;
6-tert-Butyl-4-(3,3-difluoro-pyrrolidin-1-yl)-1-(3-methyl-3H-[1,2,3]triazol-4-ylmethyl)-1H-pyrazolo[3,4-d]pyrimidine;
(S)-1-[6-tert-Butyl-1-(4-methyl-furazan-3-ylmethyl)-1H-pyrazolo[3,4-d]pyrimidin-4-yl]-pyrrolidin-3-ol; and
(S)-1-[6-tert-Butyl-1-[(2-trifluoromethylphenyl)methyl]-1H-pyrazolo[3,4-d]pyrimidin-4-yl]-pyrrolidin-3-ol.

The synthesis of the compound of formula (I) can, for example, be accomplished according to the following schemes.

Unless otherwise specified, $A^1$ to $A^3$, $R^1$ to $R^3$ and n have in the following schemes the meaning as defined above.

Following the procedure according to scheme 1, hydrazines of the general formula AA can be used as starting material. Compounds AA are either commercially available, can be synthesized by a person skilled in the art as described in the literature, or obtained as described in the experimental part.

Compound AB can be prepared from AA by reacting AA with 2-(ethoxymethylen)-propanedinitrile (CAN 123-06-8) in the presence of a base, particularly DIEA, in an inert solvent, particularly ethanol at temperatures ranging from room temperature to the boiling point of the mixture, preferably at 80-100° C.

Conversion of compound AB to AC can be achieved by hydrolysis in a suitable solvent, particularly by basic hydrolysis using a mixture of potassium hydroxide and hydrogen peroxide in dioxane-water mixtures at low temperature, particularly at 0° C. to room temperature, or by using other conditions known in the literature.

The acylation of the aromatic amine of general formula AC to give compounds of formula AE can be affected by reaction with an acylating agent AD. Acylating agents will preferably be acyl chlorides AD, particularly those that lack alpha hydrogen atoms next to the acyl group to facilitate the following condensation step to compounds of type AF. The acylation itself is achieved by methods well known to the ones skilled in the art—using e.g. acyl chlorides AD in an inert solvent like DMA, THF or mixtures thereof in the presence of a base like pyridine at temperatures between 0° C. and the reflux temperature of the solvent employed—preferably at 0° C. to room temperature.

Acyl chlorides AD are either commercially available, described in the literature, can be synthesized by a person skilled in the art or obtained as described in the experimental part.

Scheme 1

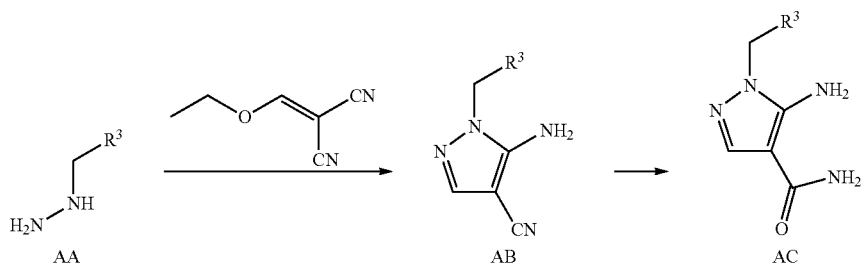

-continued

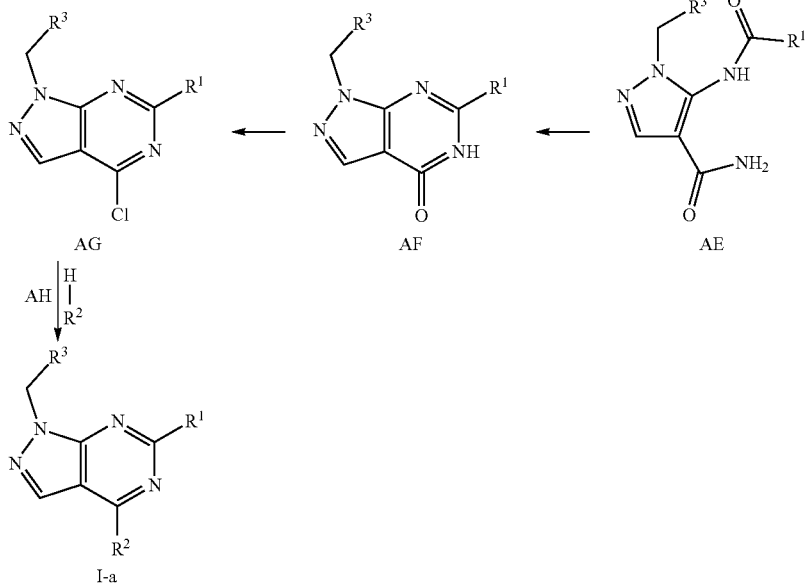

Dehydratisation and cyclisation of compounds AE gives compounds of the general formula AF. This type of reaction is well known in the art and can be done by heating compounds of type AE in the presence of a base, for example sodium hydroxide solution, either in the absence or in the presence of an inert solvent, preferably by heating to elevated temperatures like 80° C. in the absence of additional solvents.

Compounds AF can be further elaborated to compounds AG by reaction with an inorganic acid chloride, for example phosphorus oxychloride in an inert, preferably high-boiling solvent, for example N,N-diethylaniline at elevated temperatures, for example 120° C.

Coupling a compound of formula AG with a nucleophile of formula AH to give compounds with the general structure I-a is conveniently done in the presence of a base, like DIEA in an inert solvent, like DMF. The reaction can for example be effected by heating the reaction mixture to elevated temperatures for example by heating to 120° C., preferably by reaction in a microwave at 120° C.

Nucleophiles AH are either commercially available, described in the literature, can be synthesized by a person skilled in the art or obtained as described in the experimental part.

If one of the starting materials, compounds of formulae AA, AD or AH, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AA, AD or AH contain chiral centers, compounds of formula I-a can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compounds I-b (where $R^{3a}$—$CH_2$ represents a suitable protecting group) can be used as starting material for the synthesis of compounds I with other $R^1$ groups.

Compounds I-b (where $R^{3a}$—$CH_2$ represents a suitable protecting group) can be transformed to compounds BA by removal of the protecting group by methods well known in the art, for example by hydrogenation or acidic cleavage reactions. A suitable sequence starts for example with a 4-methoxybenzyl residue as $R^{3a}$—$CH_2$, that can be removed by acidic methods for example by treatment with TFA and methanesulfonic acid in an inert solvent like DCM at temperatures from 0° C. to room temperature.

Scheme 2

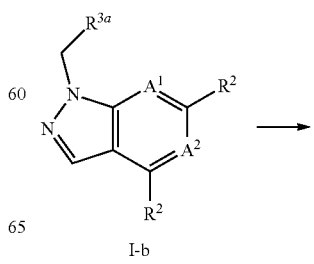

I-b

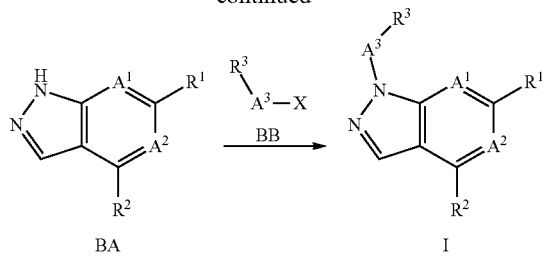

Compounds of the general formula I can be obtained from compounds of the general formula BA by nucleophilic substitution reactions on compounds of general formula BB (where X represents a leaving group on an sp3-carbon, as for example a halogen or pseudo-halogen). This reaction can be effected by methods well known in the art, for example by reacting the partners in the presence of a base, like potassium tert-butoxide, cesium carbonate or potassium carbonate in an inert solvent like acetone, DMF or DMA, for example in a microwave oven at elevated temperatures like 120° C.

Compounds of formula BB are either commercially available, described in the literature, can be synthesized by a person skilled in the art or obtained as described in the experimental part.

If one of the starting materials, compounds of formulae I-a or BB, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae I-a or BB contain chiral centers, compounds of formula I-a can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, substituted aminopyrazoles of the general formula CA can be used as starting material. Compounds CA are either commercially available, can be synthesized by a person skilled in the art as described in the literature, or obtained as described in the experimental part.

Compound CB can be prepared from CA by reacting CA with diethyl malonate (CAN 105-53-3) either with or without an inert solvent, preferably in neat diethyl malonate at elevated temperature, preferably in a microwave at 130° C.

Compounds CB can be further elaborated to compounds CC by reaction with a high boiling inorganic acid chloride, for example phenylphosphonic dichloride at elevated temperatures, for example 170° C.

Coupling a compound of formula CC with a nucleophile of formula AH to give compounds with the general structure CD is conveniently done in the presence of a base, like DIEA in an inert solvent, like DMF. The reaction can for example be effected by heating the reaction mixture to elevated temperatures for example by heating to 130° C., preferably by reaction in a microwave oven at 130° C.

Nucleophiles AH are either commercially available, described in the literature, can be synthesized by a person skilled in the art or obtained as described in the experimental part.

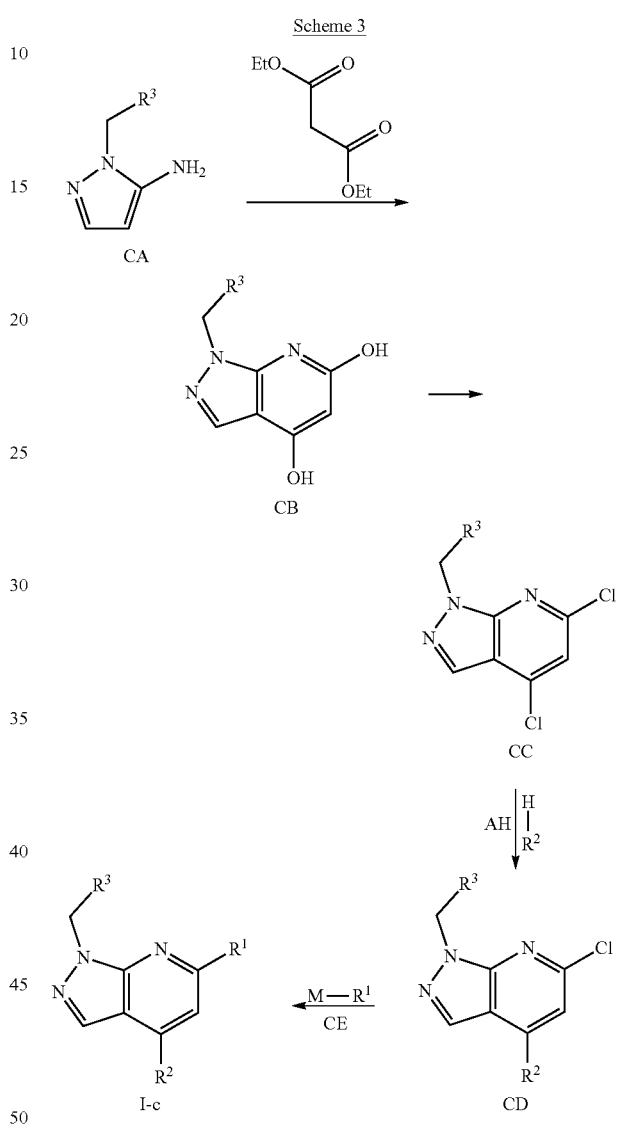

Compounds I-c can be prepared from CD by coupling a compound of formula CD with a suitably substituted alkyl, alkenyl or arylmetal species CE, particularly a cyclopropylboronic acid or cyclopropyltrifluoro-borate salt in the presence of a suitable catalyst, particularly a palladium catalyst like palladium(II)acetate in the presence of n-butyl-di-adamantylphosphine in an inert solvent such as toluene at room temperature up to the reflux temperature of the solvent in the presence of a suitable base, like cesium carbonate.

Alkyl, alkenyl or arylmetal species CE are either commercially available, described in the literature, can be synthesized by a person skilled in the art or obtained as described in the experimental part.

If one of the starting materials, compounds of formulae CA, AH or CE, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae CA, AH or CE contain chiral centers, compounds of formula I-c can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 4, compound DA (2,4,6-trichloro-3-pyridinecarboxaldehyde, CAN 1261269-66-2) can be condensed with hydrazines of general formula AA in the presence of a base, like DIEA and in an inert solvent, like THF at elevated temperatures, particularly at 50° C. to afford compounds of general formula DB together with some regioisomers of DB.

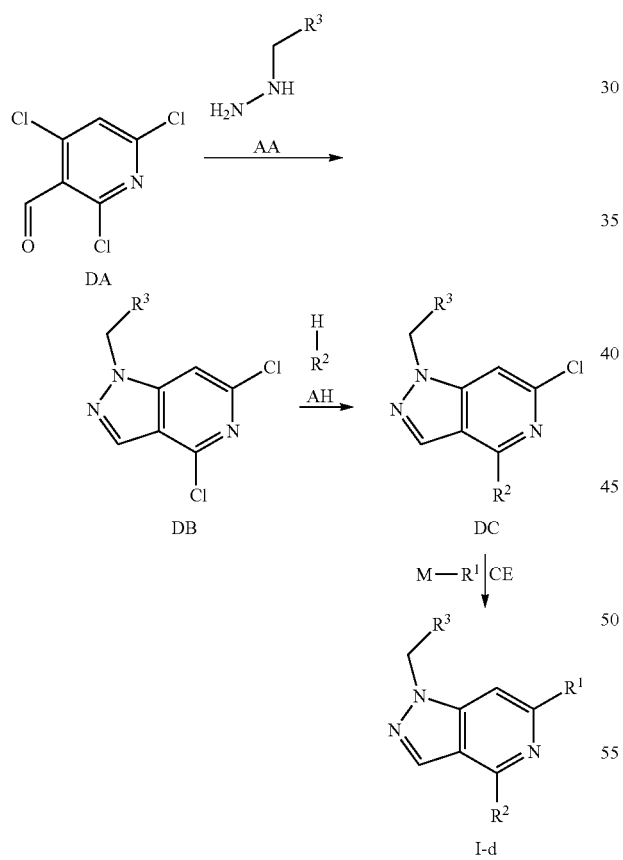

Scheme 4

Coupling a compound of formula DB with a nucleophile of formula AH to give compounds with the general structure DC is conveniently done in the presence of a base, like DIEA in an inert solvent, like DMF. The reaction can for example be affected by heating the reaction mixture to elevated temperatures for example by heating to 120° C., preferably by reaction in a microwave oven at 120° C.

Nucleophiles AH are either commercially available, described in the literature, can be synthesized by a person skilled in the art or obtained as described in the experimental part.

Compounds I-d can be prepared from DC by coupling a compound of formula DC with a suitably substituted alkyl, alkenyl or arylmetal species CE, particularly a cyclopropylboronic acid or cyclopropyltrifluoro-borate salt in the presence of a suitable catalyst, particularly a palladium catalyst like palladium(II)acetate in the presence of n-butyl-di-adamantylphosphine in an inert solvent such as toluene at room temperature up to the reflux temperature of the solvent in the presence of a suitable base, like cesium carbonate.

Alkyl, alkenyl or arylmetal species CE are either commercially available, described in the literature, can be synthesized by a person skilled in the art or obtained as described in the experimental part.

If one of the starting materials, compounds of formulae AA, AH or CE, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AA, AH or CE contain chiral centers, compounds of formula I-d can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of formula (I), comprising one of the following steps:

(a) the reaction of a compound of formula (A)

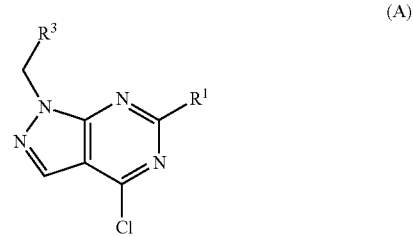

(A)

in the presence of $R^2H$ and a base;

(b) the reaction of a compound of formula (B)

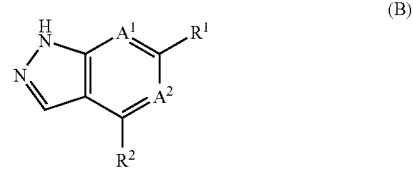

(B)

in the presence of $R^3-A^3-X$ and a base;

(c) the reaction of a compound of formula (C)

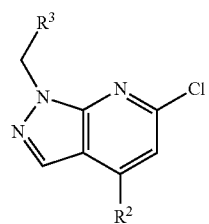

(C)

in the presence of MR$^1$, a palladium catalyst and a base;
(d) the reaction of a compound of formula (D)

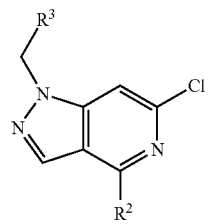

(C)

in the presence of MR$^1$, a palladium catalyst and a base;
wherein A$^1$ to A$^3$ and R$^1$ to R$^3$ are as defined above, X is a leaving group and M is a suitably substituted metal-species, like a borono-, a boryl-, a trifluoro-borate- or a stannyl species.

In step (a), the base is for example DIEA.

Step (a) is in particular advantageously carried out in an inert solvent, like DMF. Step (a) can conveniently be carried out at 120° C.

In step (b), the base is for example tert.-butoxide, cesium carbonate or potassium carbonate.

Step (b) is in particular advantageously carried out in an inert solvent, like DMF or DMA. Step (b) can conveniently be carried out at 120° C.

In step (c), the palladium catalyst is for example palladium(II)acetate. Step (c) is preferably carried out in the presence of a phosphine, in particular n-butyl-di-adamantylphosphine.

Step (c) is in particular carried out in an inert solvent, such as toluene. Step (c) can conveniently be carried out at room temperature up to reflux.

In step (c), the base is for example cesium carbonate.

MR$^1$ is advantageously a cyclopropylboronic acid or a cyclopropyltrifluoro-borate salt.

Similar conditions as for step (c) can advantageously be used for step (d).

If desired, the compound of formula (I) can be converted into a pharmaceutically acceptable salt thereof.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention particularly relates to a compound of formula (I) for the treatment or prophylaxis of myocardial infarction.

The invention further particularly relates to a compound of formula (I) for the treatment or prophylaxis of age-related macular degeneration, diabetic retinopathy, glaucoma, retinal vein occlusion, retinopathy of prematurity, ocular ischemic syndrome, geographic atrophy or uveitis.

The invention further particularly relates to a compound of formula (I) for the treatment or prophylaxis of amyotrophic lateral sclerosis or multiple sclerosis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; EI=electron ionization; ESI=electrospray; NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; DIEA=N-ethyl-N-isopropylpropan-2-amine; DBU=1,8-diazabicyclo[5.4.0]undec-7-ene; DCM=dichloromethane; DMA=dimethylacetamide; DMF=dimethylformamide; DMSO=dimethyl sulfoxide; dppf=1,1'-bis(diphenylphosphino)ferrocene; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyluronium-hexafluoro-phosphate; HPLC=LC=high performance liquid chromatography; m-CPBA=meta-chloroperoxybenzoic acid; Rt=retention time; TBAF=tetra-n-butylammonium fluoride; TBTU=O-(benzotriazol-1-yl)-N,N,N',N'-tetramethyl-uronium-tetrafluoroborate; TEMPO=2,2,6,6-tetra-methylpiperidine 1-oxyl radical; TBME32 methyl tert-butylether, THF=tetrahydrofuran; TFA=trifluoroacetic acid; tlc=thin layer chromatography; CAN=CAS Registry Number.

Example 1

6-tert-Butyl-4-(3,3-difluoro-pyrrolidin-1-yl)-[(4-methoxyphenyl)methyl]-1H-pyrazolo[3,4-d]pyrimidine a) 5-Amino-1-[(4-methoxyphenyl)methyl]-1H-pyrazole-4-carbonitrile

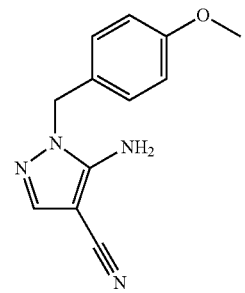 [SMILES: COc1ccc(Cn2ncc(C#N)c2N)cc1]

[(4-Methoxyphenyl)methyl]hydrazine dihydrochloride (CAN 412327-07-2, 1.0 g, 4.44 mmol), 2-(ethoxymethylene)-propanedinitrile (CAN 123-06-8, 0.542 g, 4.44 mmol) and DIEA (1.55 mL, 8.88 mmol) were combined in ethanol (7 mL) and the reaction mixture was stirred at 100° C. for 3 hours. Upon cooling in ice-water the product precipitated. Filtration, and drying gave the title compound (0.597 g, 59%) as yellow solid; LC-MS (UV peak area, ESI) 87%, 229.4 [MH$^+$].

b) 5-Amino-1-[(4-methoxyphenyl)methyl]-1H-pyrazole-4-carboxamide

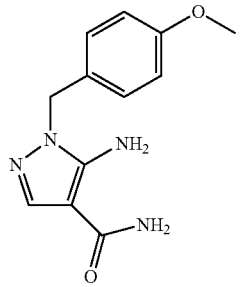 [SMILES: COc1ccc(Cn2ncc(C(N)=O)c2N)cc1]

To a solution of potassium hydroxide (1.51 g, 27 mmol) in water (15 mL) were added at 0-5° C. hydrogen peroxide (3.64 mL, 119 mmol) and a solution of 5-amino-1-[(4-methoxyphenyl)methyl]-1H-pyrazole-4-carbonitrile (0.55 g, 2.4 mmol) in dioxane (30 mL). Cooling was removed and the reaction mixture was stirred at ambient temperature for 18 hours. The mixture was partitioned between water (2×50 mL) and ethyl acetate; the organic phase was separated, dried with Na$_2$SO$_4$, filtered and concentrated in vacuo. The crude material was purified by crystallization from ethyl acetate/heptane to afford the desired product (0.51 g, 85%) as light-yellow solid; LC-MS (UV peak area, ESI) 86%, 247.5 [MH$^+$].

c) 5-(2,2-Dimethyl-propionylamino)-1-[(4-methoxyphenyl)methyl]-1H-pyrazole-4-carboxylic acid amide

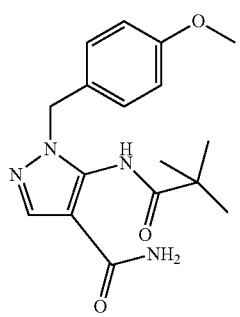 [SMILES: COc1ccc(Cn2ncc(C(N)=O)c2NC(=O)C(C)(C)C)cc1]

To a solution of 5-amino-1-[(4-methoxyphenyl)methyl]-1H-pyrazole-4-carboxamide (400 mg, 1.62 mmol) in DMA (4 mL) and THF (6 mL) was at 0° C. added pivaloyl chloride (200 µL, 1.62 mmol) and pyridine (158 µL, 1.95 mmol) and the mixture was stirred at 0° C. for 1.5 hours followed by stirring at room temperature for 2 hours. The mixture was partitioned between water (2×30 mL) and DCM; the organic phase was separated, dried with Na$_2$SO$_4$, filtered and concentrated in vacuo. The crude material was purified by flash chromatography (silica, ethyl acetate/heptane gradient) to give the desired product (1.07 g) as light-yellow oil that did still contain some DMA. The material was used in the next step without purification; LC-MS (UV peak area, ESI) 77%, 331.5 [MH$^+$].

d) 6-tert-Butyl-1,5-dihydro-1-[(4-methoxyphenyl)methyl]-4H-pyrazolo[3,4-d]pyrimidin-4-one

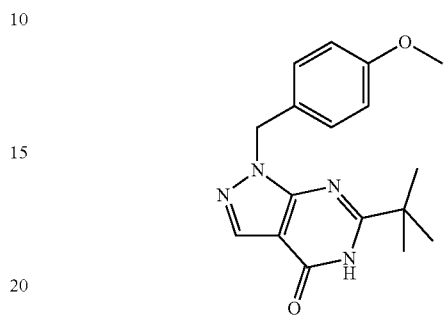

A solution of 5-(2,2-dimethyl-propionylamino)-1-[(4-methoxyphenyl)methyl]-1H-pyrazole-4-carboxylic acid amide (0.54 g, 1.63 mmol) in sodium hydroxide solution (1 N, 10 mL) was stirred at 80° C. for 2.5 hours. After cooling, water (30 mL) was added and the mixture was extracted with DCM. Organic phases were pooled, dried with Na$_2$SO$_4$, filtered and concentrated in vacuo. The crude material was purified by flash chromatography (silica, ethyl acetate/heptane gradient) to give the desired product (154 mg, 60% over two steps) as white solid; LC-MS (UV peak area, ESI) 95%, 313.5 [MH$^+$].

e) 6-tert-Butyl-4-chloro-1-[(4-methoxyphenyl)methyl]-1H-pyrazolo[3,4-d]pyrimidine

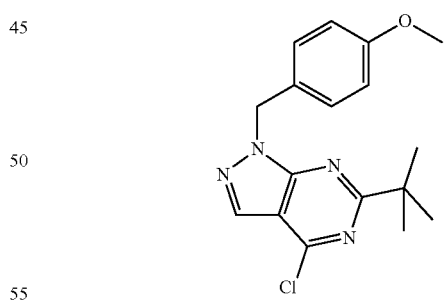

A mixture of 6-tert-butyl-1,5-dihydro-1-[(4-methoxyphenyl)methyl]-4H-pyrazolo[3,4-d]pyrimidin-4-one (0.154 g, 0.49 mmol), phosphorus oxychloride (1.57 mL, 16.9 mmol) and N,N-diethylaniline (157 µL, 0.99 mmol) was stirred at 120° C. for 4.5 hours. Phosphorus oxychloride was removed in vacuo and the residue was partitioned between water and ethyl acetate; the organic phases were pooled, dried with Na$_2$SO$_4$, filtered and concentrated in vacuo to give the desired product (144 mg) as dark green oil. The material was used in the next step without purification.

f) 6-tert-Butyl-4-(3,3-difluoro-pyrrolidin-1-yl)-1-(4-methoxy-benzyl)-1H-pyrazolo[3,4-d]pyrimidine

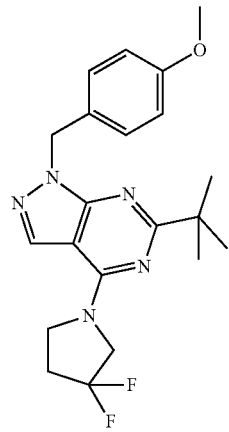 [SMILES: COc1ccc(Cn2ncc3c(N4CCC(F)(F)C4)nc(C(C)(C)C)nc32)cc1]

A mixture of 6-tert-butyl-4-chloro-1-[(4-methoxyphenyl)methyl]-1H-pyrazolo[3,4-d]pyrimidine (0.144 g, 0.44 mmol), 3,3-difluoropyrrolidine hydrochloride (62.5 mg, 0.44 mmol) and DIEA (380 μL, 2.18 mmol) in DMF (3 mL) was microwaved for 1 hour at 120° C. After cooling, the mixture was partitioned between water and ethyl acetate. Organic phases were pooled, dried with Na$_2$SO$_4$, filtered and concentrated in vacuo. The crude material was purified by flash chromatography (silica, ethyl acetate/heptane gradient) to give the desired product (174 mg, 87% over two steps) as yellow oil; LC-MS (UV peak area, ESI) 90%, 402.6 [MH$^+$].

Example 2

1-Benzyl-6-tert-butyl-4-(3,3-difluoro-pyrrolidin-1-yl)-1H-pyrazolo[3,4-d]pyrimidine

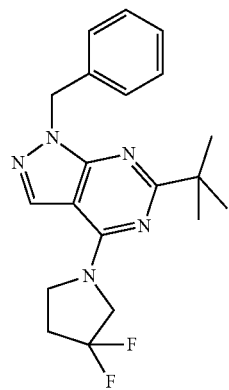 [SMILES: CC(C)(C)c1nc(N2CCC(F)(F)C2)c2cnn(Cc3ccccc3)c2n1]

The title compound was synthesized in analogy to Examples 1c to 1f, using 5-amino-1-(phenylmethyl)-1H-pyrazole-4-carboxamide (CAN 56156-22-0), pivaloyl chloride and 3,3-difluoropyrrolidine hydrochloride as starting materials, and isolated (96 mg) as yellow solid; LC-MS (UV peak area, ESI) 93%, 372.6 [MH$^+$].

Example 3

(S)-1-[6-tert-Butyl-1-[(2-chlorophenyl)methyl]-1H-pyrazolo[3,4-d]pyrimidin-4-yl]-pyrrolidin-3-ol

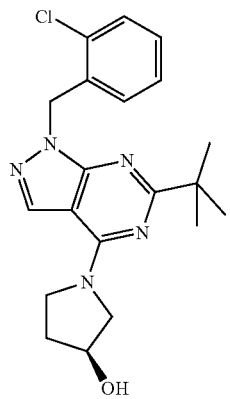 [SMILES: CC(C)(C)c1nc(N2CC[C@H](O)C2)c2cnn(Cc3ccccc3Cl)c2n1]

The title compound was synthesized in analogy to Examples 1c to 1f, using 5-amino-1-[(2-chlorophenyl)methyl]-1H-pyrazole-4-carboxamide (CAN 106898-48-0), pivaloyl chloride and (S)-3-hydroxypyrrolidine (CAN 100243-39-8) as starting materials, and isolated (2.5 mg) as colorless oil; LC-MS (ESI) 386.5 [MH$^+$].

Example 4

6-tert-Butyl-1-[(2-chlorophenyl)methyl]-4-(3,3-difluoro-pyrrolidin-1-yl)-1H-pyrazolo[3,4-d]pyrimidine

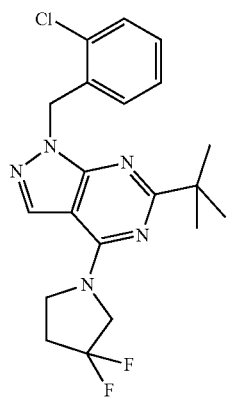 [SMILES: CC(C)(C)c1nc(N2CCC(F)(F)C2)c2cnn(Cc3ccccc3Cl)c2n1]

The title compound was synthesized in analogy to Examples 1c to 1f, using 5-amino-1-[(2-chlorophenyl)methyl]-1H-pyrazole-4-carboxamide (CAN 106898-48-0), pivaloyl chloride and 3,3-difluoropyrrolidine hydrochloride as starting materials, and isolated (16 mg) as colorless oil; LC-MS (UV peak area, ESI) 74%, 406.5 [MH$^+$].

Example 5

6-tert-Butyl-1-[(2-chlorophenyl)methyl]-4-ethoxy-1H-pyrazolo[3,4-d]pyrimidine

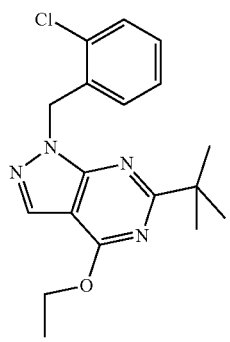 [SMILES: CCOc1nc(C(C)(C)C)nc2c1cnn2Cc1ccccc1Cl]

The title compound was synthesized in analogy to Examples 1c to 1f, using 5-amino-1-[(2-chlorophenyl)methyl]-1H-pyrazole-4-carboxamide (CAN 106898-48-0), pivaloyl chloride and ethanol as starting materials, and isolated (15 mg) as colorless oil; LC-MS (UV peak area, ESI) 83%, 345.5 [MH$^+$].

Example 6

6-tert-Butyl-1-[(2-chloro-4-fluorophenyl)methyl]-4-(3,3-difluoro-pyrrolidin-1-yl)-1H-pyrazolo[3,4-d]pyrimidine a) 6-tert-Butyl-4-(3,3-difluoro-pyrrolidin-1-yl)-1H-pyrazolo[3,4-d]pyrimidine

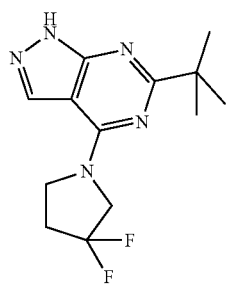 [SMILES: CC(C)(C)c1nc(N2CCC(F)(F)C2)c2cn[nH]c2n1]

To a mixture of 6-tert-butyl-4-(3,3-difluoro-pyrrolidin-1-yl)-1-(4-methoxy-benzyl)-1H-pyrazolo[3,4-d]pyrimidine (0.174 g, 0.43 mmol) and TFA (870 µL, 11.3 mmol) in DCM (3 mL) was added methanesulfonic acid (141 µL, 2.17 mmol). The mixture was stirred for 1 hour at 0° C. and for 1.5 hours at room temperature. Afterwards the mixture was rendered basic with sodium hydroxide solution (2.5 mL, 25%, cooling) and partitioned between water and DCM. Organic phases were pooled, dried with MgSO$_4$, filtered and concentrated in vacuo. The residue, 135 mg of the title compound as a light-yellow solid, was used without further purification; LC-MS (UV peak area, ESI) 80%, 282.5 [MH$^+$].

b) 6-tert-Butyl-1-(2-chloro-4-fluoro-benzyl)-4-(3,3-difluoro-pyrrolidin-1-yl)-1H-pyrazolo[3,4-d]pyrimidine

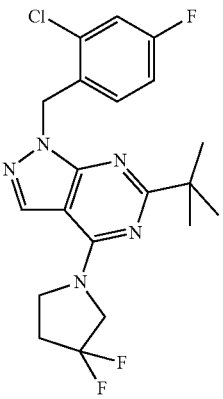 [SMILES: CC(C)(C)c1nc(N2CCC(F)(F)C2)c2cnn(Cc3ccc(F)cc3Cl)c2n1]

To a solution of 6-tert-butyl-4-(3,3-difluoro-pyrrolidin-1-yl)-1H-pyrazolo[3,4-d]pyrimidine (30 mg, 107 µmol) in acetone (1 mL) and DMF (2 mL) was added 2-chloro-1-(chloromethyl)-4-fluoro-benzene (23 mg, 128 µmol) and potassium carbonate (44 mg, 318 µmol). The mixture was microwaved for 45 minutes at 120° C., cooled and partitioned between water and ethyl acetate. Organic phases were pooled, dried by filtration over ChemElut®, and concentrated in vacuo. The residue was purified by preparative HPLC (Gemini NX, water/acetonitrile gradient), to afford the title compound (13 mg, 29%) as light-yellow oil; LC-MS (UV peak area, ESI) 78%, 424.5 [MH$^+$].

Example 7

6-tert-Butyl-4-(3,3-difluoro-pyrrolidin-1-yl)-1-[(2-trifluoromethylphenyl)methyl]-1H-pyrazolo[3,4-d]pyrimidine

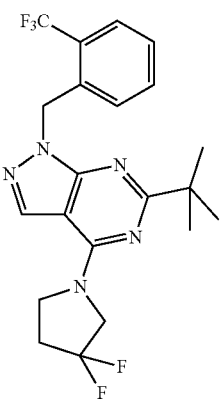 [SMILES: CC(C)(C)c1nc(N2CCC(F)(F)C2)c2cnn(Cc3ccccc3C(F)(F)F)c2n1]

The title compound was synthesized in analogy to Example 6 b, using 6-tert-butyl-4-(3,3-difluoro-pyrrolidin-1-yl)-1H-pyrazolo[3,4-d]pyrimidine (Example 6 a) and 1-(chloromethyl)-2-(trifluoromethyl)-benzene (CAN 21742-00-7) as starting materials, and isolated (7 mg, 14%) as colorless oil; MS (ESI) 440.6 [MH$^+$].

Example 8

6-tert-Butyl-4-(3,3-difluoro-pyrrolidin-1-yl)-1-phenethyl-1H-pyrazolo[3,4-d]pyrimidine

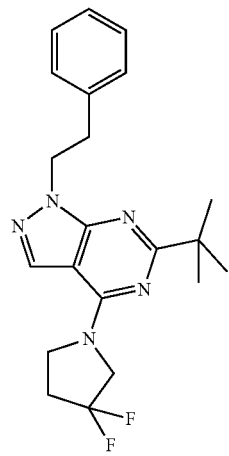 [SMILES: CC(C)(C)c1nc(N2CCC(F)(F)C2)c2cnn(CCc3ccccc3)c2n1]

The title compound was synthesized in analogy to Example 6 b, using 6-tert-butyl-4-(3,3-difluoro-pyrrolidin-1-yl)-1H-pyrazolo[3,4-d]pyrimidine (Example 6 a) and (2-bromoethyl)-benzene (CAN 103-63-9) as starting materials, and isolated (10 mg, 24%) as colorless oil; MS (ESI) 386.6 [MH⁺].

Example 9

6-tert-Butyl-4-(3,3-difluoro-pyrrolidin-1-yl)-1-(4-methyl-furazan-3-ylmethyl)-1H-pyrazolo[3,4-d]pyrimidine

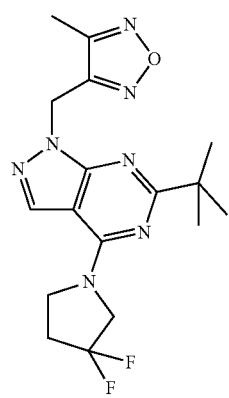 [SMILES: Cc1nonc1Cn1ncc2c(N3CCC(F)(F)C3)nc(C(C)(C)C)nc21]

To a solution of 6-tert-butyl-4-(3,3-difluoro-pyrrolidin-1-yl)-1H-pyrazolo[3,4-d]pyrimidine (Example 6 a, 30 mg, 107 µmol) in THF (0.3 mL) and DMA (0.5 mL) was added 3-(chloromethyl)-4-methyl-1,2,5-oxadiazole (28 mg, 213 µmol) and potassium tert-butoxide (24 mg, 213 µmol). The mixture was microwaved for 20 minutes at 110° C., cooled and partitioned between water and ethyl acetate. Organic phases were pooled, dried by filtration over ChemElut®, and concentrated in vacuo. The residue was purified by preparative HPLC (Gemini NX, water/acetonitrile gradient), to afford the title compound (6 mg, 14%) as light-yellow oil; LC-MS (UV peak area, ESI) 94.9%, 378.1855 [MH⁺].

Example 10

6-tert-Butyl-4-(3,3-difluoro-pyrrolidin-1-yl)-1-(2-methanesulfonyl-benzyl)-1H-pyrazolo[3,4-d]pyrimidine

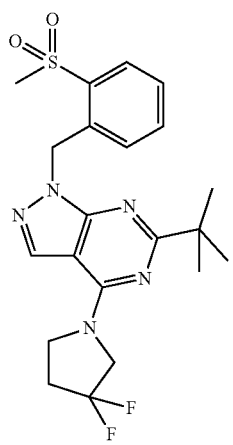 [SMILES: CC(C)(C)c1nc(N2CCC(F)(F)C2)c2cnn(Cc3ccccc3S(C)(=O)=O)c2n1]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 1-(chloromethyl)-2-(methylsulfonyl)-benzene (CAN 168551-51-7) as starting materials, and isolated (6 mg, 12%) as colorless oil; LC-MS (UV peak area, ESI) 89.3%, 450.1776 [MH⁺].

Example 11

6-tert-Butyl-4-(3,3-difluoro-pyrrolidin-1-yl)-1-(2-pyridin-3-yl-ethyl)-1H-pyrazolo[3,4-d]pyrimidine

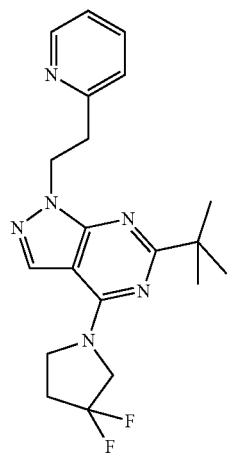 [SMILES: CC(C)(C)c1nc(N2CCC(F)(F)C2)c2cnn(CCc3ccccn3)c2n1]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 2-(2- bromoethyl)-pyridine (CAN 39232-04-7) as starting materials, and isolated (6 mg, 12%) as colorless oil; MS (ESI) 387.6 [MH⁺].

Example 12

6-tert-Butyl-1-(2-chloro-pyridin-3-ylmethyl)-4-(3,3-difluoro-pyrrolidin-1-yl)-1H-pyrazolo[3,4-d]pyrimidine

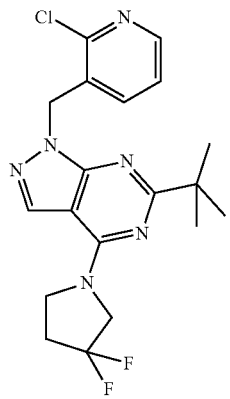 [SMILES: CC(C)(C)c1nc(N2CCC(F)(F)C2)c2cnn(Cc3cccnc3Cl)c2n1]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 2-chloro-3-(chloromethyl)-pyridine (CAN 89581-84-0) as starting materials, and isolated (24 mg, 55%) as colorless oil; MS (ESI) 407.5 [MH⁺].

Example 13

6-tert-Butyl-4-(3,3-difluoro-pyrrolidin-1-yl)-1-(1,1-dioxo-1λ⁶-thietan-3-yl)-1H-pyrazolo[3,4-d]pyrimidine

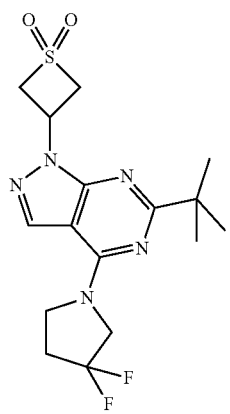 [SMILES: CC(C)(C)c1nc(N2CCC(F)(F)C2)c2cnn(C3CS(=O)(=O)C3)c2n1]

To a solution of 6-tert-butyl-4-(3,3-difluoro-pyrrolidin-1-yl)-1H-pyrazolo[3,4-d]pyrimidine (Example 6 a, 30 mg, 107 µmol) in THF (0.3 mL) and DMF (0.3 mL) was added 3-chloro-thietane 1,1-dioxide (CAN 15953-83-0, 30 mg, 213 µmol), DIEA (33.5 µL, 192 µmol) and potassium tert-butoxide (24 mg, 213 µmol). The mixture was stirred for 1 hour at 0° C. and for 1 hour at room temperature and partitioned between water and ethyl acetate. Organic phases were pooled, dried by filtration over ChemElut®, and concentrated in vacuo. The residue was purified by preparative HPLC (Gemini NX, water/acetonitrile gradient), to afford the title compound (25 mg, 60%) as light-yellow oil; LC-MS (UV peak area, ESI) 97.7%, 386.1462 [MH⁺].

Example 14

6-tert-Butyl-4-(3,3-difluoro-pyrrolidin-1-yl)-1-(tetrahydro-furan-3-yl)-1H-pyrazolo[3,4-d]pyrimidine

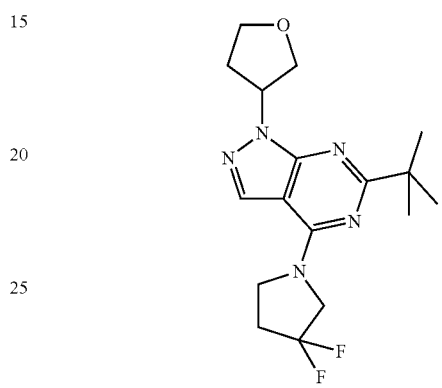

The title compound was synthesized in analogy to Example 9, using 6-tert-butyl-4-(3,3-difluoro-pyrrolidin-1-yl)-1H-pyrazolo[3,4-d]pyrimidine (Example 6 a) and 3-chlorotetrahydro-furan (CAN 19311-38-7) as starting materials, and isolated (1.4 mg, 4.5%) as yellow oil; MS (ESI) 352.4 [MH⁺].

Example 15

6-tert-Butyl-4-(3,3-difluoro-pyrrolidin-1-yl)-1-(1-methyl-1H-tetrazol-5-ylmethyl)-1H-pyrazolo[3,4-d]pyrimidine

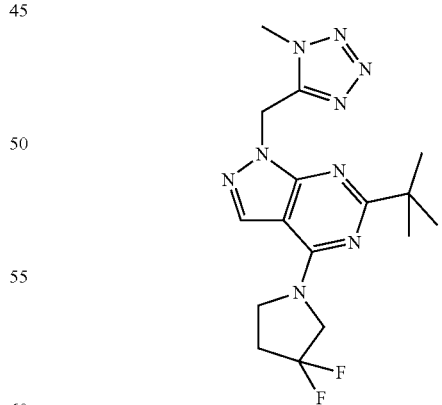

The title compound was synthesized in analogy to Example 9, using 6-tert-butyl-4-(3,3-difluoro-pyrrolidin-1-yl)-1H-pyrazolo[3,4-d]pyrimidine (Example 6 a) and 5-(chloromethyl)-1-methyl-1H-tetrazole (CAN 57235-84-4) as starting materials, and isolated (52 mg, 43%) as white solid; LC-MS (UV peak area, ESI) 100%, 378.1961 [MH⁺].

Example 16

6-tert-Butyl-1-(1-cyclopropyl-1H-tetrazol-5-ylmethyl)-4-(3,3-difluoro-pyrrolidin-1-yl)-1H-pyrazolo[3,4-d]pyrimidine

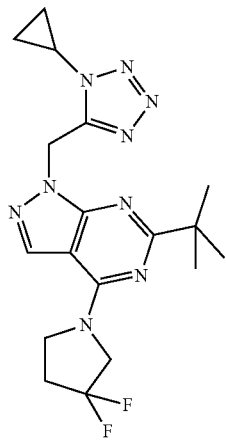 [SMILES: CC(C)(C)c1nc(N2CCC(F)(F)C2)c2cnn(Cc3nnnn3C3CC3)c2n1]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 5-(chloromethyl)-1-cyclopropyl-1H-tetrazole (CAN 949980-56-7) as starting materials and cesium carbonate as base, and isolated (2 mg, 3.7%) as yellow oil; LC-MS (UV peak area, ESI) 91.8%, 404.2114 [MH$^+$].

Example 17

6-tert-Butyl-4-(3,3-difluoro-pyrrolidin-1-yl)-1-(4,5-dimethyl-4H-[1,2,4]triazol-3-ylmethyl)-1H-pyrazolo[3,4-d]pyrimidine

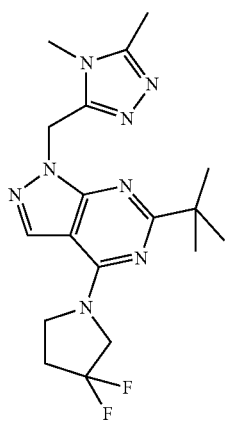 [SMILES: Cc1nnc(Cn2ncc3c(N4CCC(F)(F)C4)nc(C(C)(C)C)nc32)n1C]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 3-(chloromethyl)-4,5-dimethyl-4H-1,2,4-triazole (CAN 881845-16-5) as starting materials, cesium carbonate as base, and isolated (2 mg, 4.8%) as yellow oil; LC-MS (UV peak area, ESI) 76.6%, 391.2168 [MH$^+$].

Example 18

6-tert-Butyl-1-(4,5-dimethyl-4H-[1,2,4]triazol-3-ylmethyl)-4-(3-fluoro-2,5-dihydro-pyrrol-1-yl)-1H-pyrazolo[3,4-d]pyrimidine

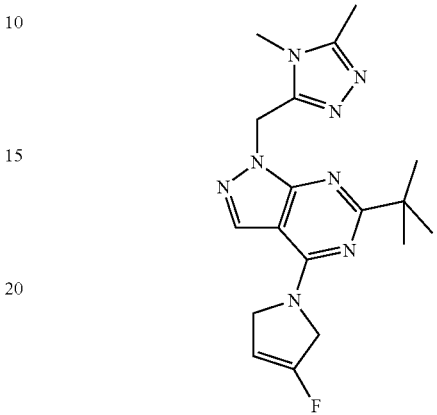

The title compound was isolated as side product during preparation of Example 17, and isolated (4.9 mg, 12.4%) as yellow oil; LC-MS (UV peak area, ESI) 91.7%, 371.2107 [MH$^+$].

Example 19

6-tert-Butyl-4-(3,3-difluoro-pyrrolidin-1-yl)-1-(3-methyl-3H-[1,2,3]triazol-4-ylmethyl)-1H-pyrazolo[3,4-d]pyrimidine

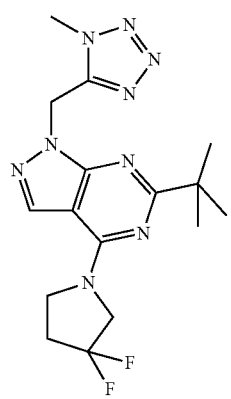 [SMILES: Cn1nnnc1Cn1ncc2c(N3CCC(F)(F)C3)nc(C(C)(C)C)nc21]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 5-(chloromethyl)-1-methyl-1H-1,2,3-triazole hydrochloride (1:1) (CAN 327985-59-1) as starting materials, and cesium carbonate as base, and isolated (3 mg, 7.9%) as yellow oil; LC-MS (UV peak area, ESI) 89.5%, 377.2007 [MH$^+$].

Example 20

6-tert-Butyl-4-(3-fluoro-2,5-dihydro-pyrrol-1-yl)-1-(3-methyl-3H-[1,2,3]triazol-4-ylmethyl)-1H-pyrazolo[3,4-d]pyrimidine

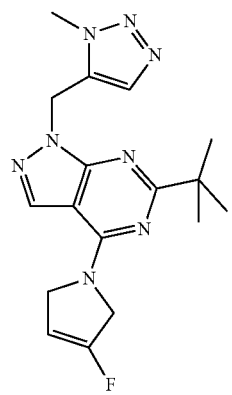 [SMILES: Cn1nncc1Cn1ncc2c(N3CC=C(F)C3)nc(C(C)(C)C)nc21]

The title compound was isolated as side product during preparation of Example 17, and isolated (6 mg, 14.9%) as yellow oil; LC-MS (UV peak area, ESI) 84.5%, 357.1948 [MH$^+$].

Example 21

2-[6-tert-Butyl-4-(3,3-difluoro-pyrrolidin-1-yl)-pyrazolo[3,4-d]pyrimidin-1-yl]-1-pyridin-4-yl-ethanone

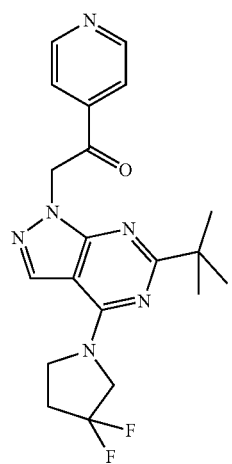 [SMILES: CC(C)(C)c1nc(N2CCC(F)(F)C2)c2cnn(CC(=O)c3ccncc3)c2n1]

The title compound was synthesized in analogy to Example 9, using 6-tert-butyl-4-(3,3-difluoro-pyrrolidin-1-yl)-1H-pyrazolo[3,4-d]pyrimidine (Example 6 a) and 2-bromo-1-(4-pyridinyl)-ethanone hydrobromide (1:1) (CAN 5349-17-7) as starting materials, and isolated (3.3 mg, 4.6%) as yellow oil; MS (ESI) 100%, 401.0 [MH$^+$].

Example 22

2-[6-tert-Butyl-4-(3,3-difluoro-pyrrolidin-1-yl)-pyrazolo[3,4-d]pyrimidin-1-yl]-1-pyridin-2-yl-ethanone

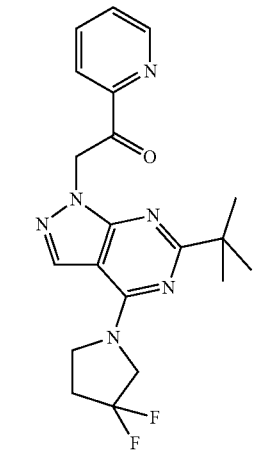

The title compound was synthesized in analogy to Example 9, using 6-tert-butyl-4-(3,3-difluoro-pyrrolidin-1-yl)-1H-pyrazolo[3,4-d]pyrimidine (Example 6 a) and 2-bromo-1-(2-pyridinyl)-ethanone hydrobromide (1:1) (CAN 17570-98-8) as starting materials, and isolated (2.0 mg, 2.8%) as brown oil; MS (ESI) 100%, 401.0 [MH$^+$].

Example 23

(S)-1-[6-tert-Butyl-1-[(4-methoxyphenyl)methyl]-1H-pyrazolo[3,4-d]pyrimidin-4-yl]-pyrrolidin-3-ol

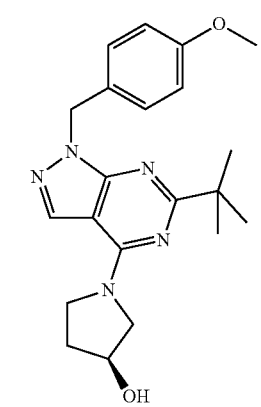 [SMILES: COc1ccc(Cn2ncc3c(N4CC[C@H](O)C4)nc(C(C)(C)C)nc32)cc1]

The title compound was synthesized in analogy to Example 1f, using 6-tert-butyl-4-chloro-1-[(4-methoxyphenyl)methyl]-1H-pyrazolo[3,4-d]pyrimidine (Example 1e, 847 mg, 2.56 mmol) and (3S)-3-pyrrolidinol (CAN 100243-39-8; 639 µL, 7.68 mmol) as starting materials and isolated (1.08 g, quant.) as white foam; LC-MS (UV peak area, ESI) 96%, 382.7 [MH$^+$].

Example 24

6-Cyclopropyl-4-(3,3-difluoro-pyrrolidin-1-yl)-1-[(4-methoxyphenyl)methyl]-1H-pyrazolo[3,4-b]pyridine a) 1-[(4-Methoxyphenyl)methyl]-1H-pyrazolo[3,4-b]pyridine-4,6-diol

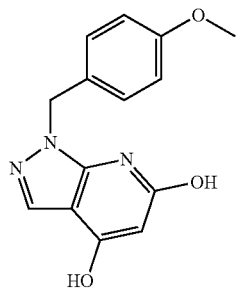 [SMILES: COc1ccc(Cn2ncc3c(O)cc(O)nc32)cc1]

1-[(4-Methoxyphenyl)methyl]-1H-pyrazol-5-amine (CAN 3528-45-8, 2.0 g, 9.84 mmol), and diethyl malonate (25 mL, 164 mmol) were stirred for 15 minutes at room temperature and subsequently warmed in a microwave oven for 3 hours to 130° C. After cooling the solid product was filtered off and dried to yield the title compound (1.25 g, 47%) as light yellow solid; MS (ESI) 272.5 [MH$^+$].

b) 4,6-Dichloro-1-[(4-methoxyphenyl)methyl]-1H-pyrazolo[3,4-b]pyridine

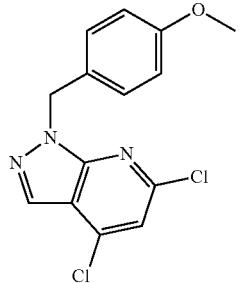 [SMILES: COc1ccc(Cn2ncc3c(Cl)cc(Cl)nc32)cc1]

A mixture of 1-[(4-methoxyphenyl)methyl]-1H-pyrazolo[3,4-b]pyridine-4,6-diol (0.9 g, 3.32 mmol) and phenylphosphonic dichloride (7 mL, 49.9 mmol) was stirred at 170° C. for 20 hours. After cooling, the mixture was diluted with DCM (100 mL), basicified with 25% sodium hydroxide in ice water and partitioned into DCM (3×100 mL); the organic phase was separated, dried with MgSO$_4$, filtered and concentrated in vacuo. The crude material was purified by flash chromatography (silica, ethyl acetate/DCM gradient) to afford the desired product (0.365 g, 36%) as light-yellow solid; MS (ESI) 308.4, 310.4 [MH$^+$].

c) 6-Chloro-4-(3,3-difluoro-pyrrolidin-1-yl)-1-[(4-methoxyphenyl)phenyl]-1H-pyrazolo[3,4-b]pyridine

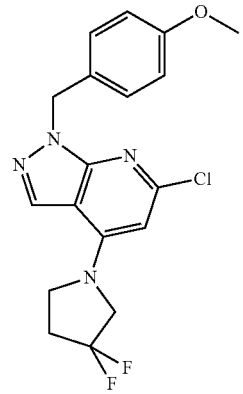 [SMILES: COc1ccc(Cn2ncc3c(N4CCC(F)(F)C4)cc(Cl)nc32)cc1]

To a solution of 4,6-dichloro-1-[(4-methoxyphenyl)methyl]-1H-pyrazolo[3,4-b]pyridine (365 mg, 1.18 mmol) in DMA (3 mL) was added 3,3-difluoropyrrolidine hydrochloride (340 mg, 2.37 mmol) and DIEA (2.07 mL, 11.8 mmol) and the mixture was warmed in a microwave oven to 130° C. for 1 hour. The mixture was partitioned between water and TBME; the organic phases were pooled, dried with MgSO$_4$, filtered and concentrated in vacuo. The crude material was recrystallized from an ethyl acetate/heptane mixture to give the desired product (279 mg, 62%) as off-white solid; MS (ESI) 379.5 [MH$^+$].

d) 6-Cyclopropyl-4-(3,3-difluoro-pyrrolidin-1-yl)-1-[(4-methoxyphenyl)methyl]-1H-pyrazolo[3,4-b]pyridine

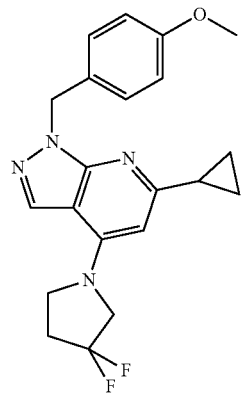 [SMILES: COc1ccc(Cn2ncc3c(N4CCC(F)(F)C4)cc(C4CC4)nc32)cc1]

To a solution of 6-chloro-4-(3,3-difluoro-pyrrolidin-1-yl)-1-[(4-methoxyphenyl)phenyl]-1H-pyrazolo[3,4-b]pyridine (100 mg, 264 µmol), potassium cyclopropyltrifluoroborate (78.1 mg, 528 µmol) and cesium carbonate (258 mg, 792 µmol) in toluene (1.55 mL) and water (0.21 mL) was added Pd(OAc)$_2$ (5.9 mg, 26.4 µmol) and butyl-bis(tricyclo[3.3.1.1$^{3.7}$]dec-1-yl)-phosphine (9.5 mg, 26.4 µmol). The mixture was stirred at 100° C. for 6 hours and after cooling, passed through a Chemelut® cartridge and concentrated in vacuo. The crude material was purified by flash chromatography (silica, ethyl acetate/heptane gradient) to give the desired product (36 mg, 31%) as yellow solid; MS (ESI) 385.6 [MH⁺].

Example 25

(S)-1-[6-tert-Butyl-1-(4-methyl-furazan-3-ylmethyl)-1H-pyrazolo[3,4-d]pyrimidin-4-yl]-pyrrolidin-3-ol a) (S)-1-(6-tert-Butyl-1H-pyrazolo[3,4-d]pyrimidin-4-yl)-pyrrolidin-3-ol

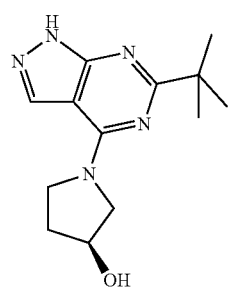 [SMILES: CC(C)(C)c1nc(N2CC[C@H](O)C2)c2cn[nH]c2n1]

To a solution of (S)-1-[6-tert-butyl-1-(4-methoxy-benzyl)-1H-pyrazolo[3,4-d]pyrimidin-4-yl]-pyrrolidin-3-ol (Example 23, 890 mg, 2.33 mmol) in DCM (50 mL) was added at 0° C. TFA (3 mL, 38.9 mmol) and methanesulfonic acid (0.6 mL, 9.24 mmol). The mixture was kept in the fridge for 3 days and concentrated in vacuo. The residue was partitioned between ethyl acetate and ice-cold sodium hydroxide solution (25%, 10 mL). Organic phases were pooled, dried with Na₂SO₄, filtered and concentrated in vacuo. The crude material was purified by flash chromatography (silica, ethyl acetate/heptane gradient) to afford the desired product (0.67 g, quant.) as white solid; LC-MS (UV peak area, ESI) 98.2%, 262.1670 [MH⁺].

b) 6-tert-Butyl-4-[(S)-3-(tert-butyl-dimethyl-silanyloxy)-pyrrolidin-1-yl]-1H-pyrazolo[3,4-d]pyrimidine

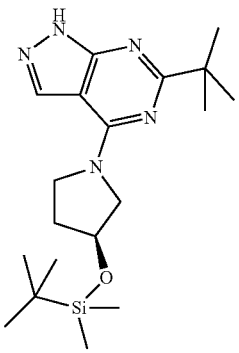 [SMILES: CC(C)(C)c1nc(N2CC[C@H](O[Si](C)(C)C(C)(C)C)C2)c2cn[nH]c2n1]

To a solution of (S)-1-(6-tert-butyl-1H-pyrazolo[3,4-d]pyrimidin-4-yl)-pyrrolidin-3-ol (576 mg, 2.2 mmol) and imidazole (300 mg, 4.41 mmol) in DMF (10 mL) was added a solution of tert-butyldimethylchlorosilane (664 mg, 4.41 mmol) in DMF (10 mL) during 30 minutes. The mixture was stirred at room temperature for 20 hours and afterwards concentrated in vacuo. The residue was partitioned between water (25 mL) and DCM (2×50 mL); the organic phases were pooled, dried with MgSO₄, filtered and concentrated in vacuo. The crude material was purified by flash chromatography (silica, ethyl acetate/heptane gradient) to afford the desired product (0.445 g, 54%) as white solid; LC-MS (UV peak area, ESI) 99%, 376.6 [MH⁺].

c) 6-tert-Butyl-4-[(S)-3-(tert-butyl-dimethyl-silanyloxy)-pyrrolidin-1-yl]-1-(4-methyl-furazan-3-ylmethyl)-1H-pyrazolo[3,4-d]pyrimidine

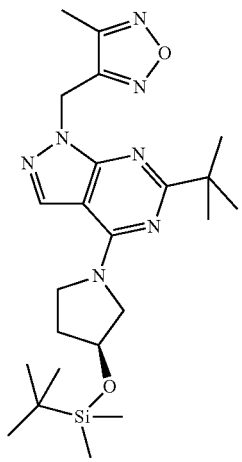 [SMILES: Cc1nonc1Cn1ncc2c(N3CC[C@H](O[Si](C)(C)C(C)(C)C)C3)nc(C(C)(C)C)nc21]

To a solution of 6-tert-butyl-4-[(S)-3-(tert-butyl-dimethyl-silanyloxy)-pyrrolidin-1-yl]-1H-pyrazolo[3,4-d]pyrimidine (70 mg, 186 µmol) in DMA (2 mL) was added 3-(chloromethyl)-4-methyl-1,2,5-oxadiazole (39.5 mg, 238 µmol) and potassium tert-butoxide (41.8 mg, 373 µmol). The mixture was microwaved for 30 minutes at 150° C., cooled and partitioned between water and ethyl acetate. Organic phases were pooled, dried by filtration over ChemElut®, and concentrated in vacuo. The residue was purified by preparative HPLC (Gemini NX, water/acetonitrile gradient), to afford the title compound (20 mg, 23%) as light-yellow oil; LC-MS (UV peak area, ESI) 99.6%, 472.2873 [MH⁺].

d) (S)-1-[6-tert-Butyl-1-(4-methyl-furazan-3-ylmethyl)-1H-pyrazolo[3,4-d]pyrimidin-4-yl]-pyrrolidin-3-ol

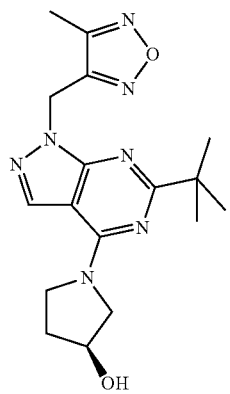 [SMILES: Cc1nonc1Cn1ncc2c(N3CC[C@H](O)C3)nc(C(C)(C)C)nc21]

To a solution of 6-tert-butyl-4-[(S)-3-(tert-butyl-dimethyl-silanyloxy)-pyrrolidin-1-yl]-1-(4-methyl-furazan-3-ylmethyl)-1H-pyrazolo[3,4-d]pyrimidine (20 mg, 42.4 μmol in THF (1 mL) was added TBAF (170 μL mg, 170 μmol). The mixture was stirred at room temperature for 2 hours and afterwards, passed through a Chemelut® cartridge and concentrated in vacuo. The crude material was purified by flash chromatography (silica, ethyl acetate) to give the desired product (13 mg, 86%) as yellowish foam; MS (ESI) 358.7 [MH+].

Example 26

6-tert-Butyl-4-[(S)-3-(4-methyl-furazan-3-yl-methoxy)-pyrrolidin-1-yl]-1-(4-methyl-furazan-3-ylmethyl)-1H-pyrazolo[3,4-d]pyrimidine

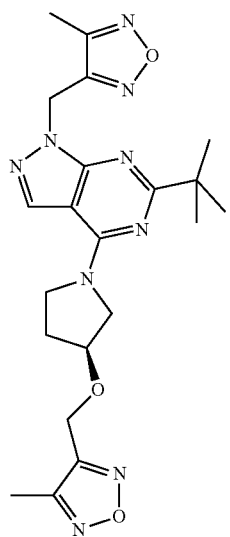 [SMILES: Cc1nonc1CO[C@H]1CCN(c2nc(C(C)(C)C)nc3c2cnn3Cc2nonc2C)C1]

The title compound was isolated as side-product in Example 26 c (4.4 mg, 5.2%) as colorless wax; LC-MS (UV peak area, ESI) 93.2%, 454.2312 [MH+].

Example 27

6-Cyclopropyl-4-(3,3-difluoro-pyrrolidin-1-yl)-1-(4-methyl-furazan-3-ylmethyl)-1H-pyrazolo[4,3-c]pyridine a) 4,6-Dichloro-1-[(4-methoxyphenyl)methyl]-1H-pyrazolo[4,3-c]pyridine

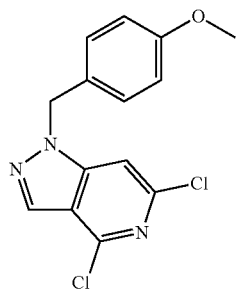 [SMILES: COc1ccc(Cn2ncc3c(Cl)nc(Cl)cc32)cc1]

To a solution of 2,4,6-trichloro-3-pyridinecarboxaldehyde (CAN 1261269-66-2, 375 mg, 178 mmol) and DIEA (1.56 mL, 8.91 mmol) in THF (4.0 mL) at 50° C. was added with stirring a solution of [(4-methoxyphenyl)methyl]-hydrazine hydrochloride (1:1) (370 mg, 1.96 mmol) in THF (4.0 mL). The mixture was stirred for 20 minutes at 50° C., cooled and partitioned between ethyl acetate and water. Organic phases were pooled, dried with $Na_2SO_4$, filtered and concentrated in vacuo. The crude material was purified by flash chromatography (silica, ethyl acetate/heptane gradient) to afford the desired product (0.21 g, 38%) as white solid; LC-MS (UV peak area, ESI) 86.4%, 308.0358, 310.0328 [MH+].

b) 6-Chloro-4-(3,3-difluoro-pyrrolidin-1-yl)-1-[(4-methoxyphenyl)methyl]-1H-pyrazolo[4,3-c]pyridine

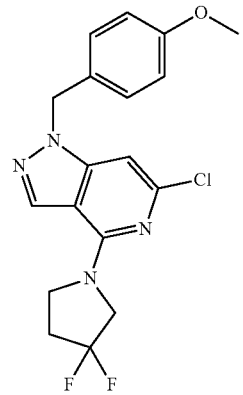 [SMILES: COc1ccc(Cn2ncc3c(N4CCC(F)(F)C4)nc(Cl)cc32)cc1]

To a solution of 4,6-dichloro-1-[(4-methoxyphenyl)methyl]-1H-pyrazolo[4,3-c]pyridine (185 mg, 0.6 mmol) and DIEA (839 μL, 4.8 mmol) in DMF (2 mL) was added 3,3-difluoropyrrolidine hydrochloride (129 mg, 0.9 mmol). The mixture was warmed in the microwave oven for 1 hour at 120° C., cooled and partitioned between water and ethyl acetate. The organic phases were pooled, dried with $MgSO_4$, filtered and concentrated in vacuo. The crude material was purified by flash chromatography (silica, ethyl acetate/heptane gradient) to afford the desired product (186 mg, 82%) as yellow solid; LC-MS (UV peak area, ESI) 97.4%, 379.1133 [MH+].

c) 6-Cyclopropyl-4-(3,3-difluoro-pyrrolidin-1-yl)-1-[(4-methoxyphenyl)methyl]-1H-pyrazolo[4,3-c]pyridine

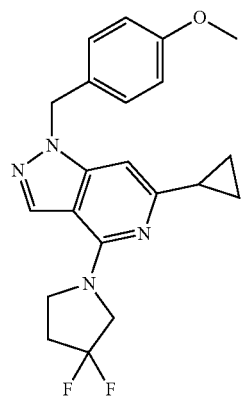 [SMILES: COc1ccc(Cn2ncc3c(N4CCC(F)(F)C4)nc(C4CC4)cc32)cc1]

To a solution of 6-chloro-4-(3,3-difluoro-pyrrolidin-1-yl)-1-[(4-methoxyphenyl)methyl]-1H-pyrazolo[4,3-c]pyridine (120 mg, 317 µmol), potassium cyclopropyltrifluoroborate (141 mg, 950 µmol) and cesium carbonate 310 mg, 950 µmol) in toluene (0.8 mL) and water (0.1 mL) was added Pd(OAc)$_2$ (7.1 mg, 31.7 µmol) and butyl-bis(tricyclo[3.3.1.1$^{3,7}$]dec-1-yl)-phosphine (11.4 mg, 31.7 µmol). The mixture was stirred at 110° C. for 5 hours and after cooling, passed through a Chemelut® cartridge and concentrated in vacuo. The crude material was purified by flash chromatography (silica, ethyl acetate/heptane gradient) to give the desired product (116 mg, 85%) as yellow wax; MS (ESI) 385.6 [MH$^+$].

d) 6-Cyclopropyl-4-(3,3-difluoro-pyrrolidin-1-yl)-1H-pyrazolo[4,3-c]pyridine

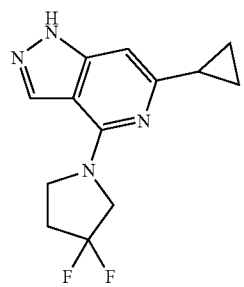 [SMILES: FC1(F)CCN(c2nc(C3CC3)cc3[nH]ncc23)C1]

To a solution of 6-cyclopropyl-4-(3,3-difluoro-pyrrolidin-1-yl)-1-[(4-methoxyphenyl)methyl]-1H-pyrazolo[4,3-c]pyridine (116 mg, 302 µmol) in DCM (1.5 mL) was added at 0° C. TFA (395 µL, 5.1 mmol) and methanesulfonic acid (78.4 µL, 1.21 mmol). The mixture was stirred at 0° C. for 1 hour, at room temperature overnight and for 3 hours at 40° C. After cooling 25% sodium hydroxide in ice water was added, the mixture was dried by extraction over Chemelut® and concentrated in vacuo. The crude material was purified by flash chromatography (silica, ethyl acetate/heptane gradient) to afford the desired product (81 mg, quant.) as brown solid; MS (ESI) 265.6 [MH$^+$].

e) 6-Cyclopropyl-4-(3,3-difluoro-pyrrolidin-1-yl)-1-(4-methyl-furazan-3-ylmethyl)-1H-pyrazolo[4,3-c]pyridine

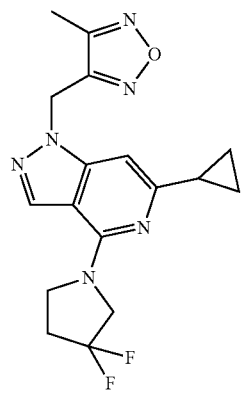 [SMILES: Cc1nonc1Cn1ncc2c(N3CCC(F)(F)C3)nc(C3CC3)cc21]

The title compound was synthesized in analogy to Example 9, using 6-cyclopropyl-4-(3,3-difluoro-pyrrolidin-1-yl)-1H-pyrazolo[4,3-c]pyridine (Example 27 d, 81 mg, 307 µmol) and 3-(chloromethyl)-4-methyl-1,2,5-oxadiazole (81.3 mg, 613 µmol) as starting materials, and isolated (23 mg, 21%) as yellow oil; LC-MS (UV peak area, ESI) 99.2%, 361.1591 [MH$^+$].

Example 28

6-Cyclopropyl-4-(3,3-difluoro-pyrrolidin-1-yl)-1-(4-methyl-furazan-3-ylmethyl)-1H-pyrazolo[3,4-b]pyridine a) 6-Cyclopropyl-4-(3,3-difluoro-pyrrolidin-1-yl)-1H-pyrazolo[3,4-b]pyridine

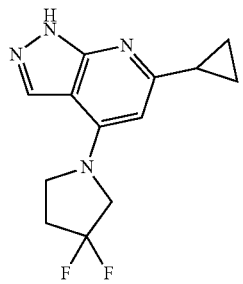 [SMILES: FC1(F)CCN(c2cc(C3CC3)nc3[nH]ncc23)C1]

The title compound was synthesized in analogy to Example 27 d, using 6-cyclopropyl-4-(3,3-difluoro-pyrrolidin-1-yl)-1-[(4-methoxyphenyl)methyl]-1H-pyrazolo[3,4-b]pyridine (Example 24 d, 90 mg, 234 µmol) as starting material, and isolated (63 mg, quant.) as yellow oil; and used without further characterization in the next step.

b) 6-Cyclopropyl-4-(3,3-difluoro-pyrrolidin-1-yl)-1-(4-methyl-furazan-3-ylmethyl)-1H-pyrazolo[3,4-b]pyridine

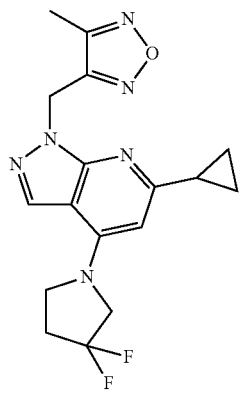 [SMILES: Cc1nonc1Cn1ncc2c(N3CCC(F)(F)C3)cc(C3CC3)nc21]

The title compound was synthesized in analogy to Example 9, using 6-cyclopropyl-4-(3,3-difluoro-pyrrolidin-1-yl)-1H-pyrazolo[3,4-b]pyridine (Example 28 a, 79 mg, 299 µmol) and 3-(chloromethyl)-4-methyl-1,2,5-oxadiazole (79.2 mg, 598 µmol) as starting materials, and isolated (5.6 mg, 4.2%) as brown oil; LC-MS (UV peak area, ESI) 95.1%, 361.1585 [MH$^+$].

Example 29

(S)-1-[6-tert-Butyl-1-[(2-trifluoromethylphenyl)methyl]-1H-pyrazolo[3,4-d]pyrimidin-4-yl]pyrrolidin-3-ol a) 5-Amino-1-[(2-trifluoromethylphenyl)methyl]-1H-pyrazole-4-carbonitrile

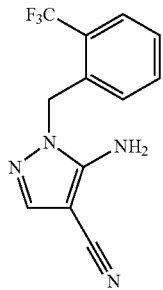 [SMILES: N#Cc1cnn(Cc2ccccc2C(F)(F)F)c1N]

The title compound was synthesized in analogy to Example 1 a, using [[2-(trifluoromethyl)phenyl]methyl]-hydrazine hydrochloride (1:1) (CAN 1263378-37-5, 1.0 g, 4.28 mmol) and 2-(ethoxymethylene)-propanedinitrile (CAN 123-06-8, 533 mg, 4.28 mmol) as starting materials, and isolated (855 mg, 75%) as yellow solid; MS (ESI) 267.5 [MH+].

b) 5-Amino-1-[(2-trifluoromethylphenyl)methyl]-1H-pyrazole-4-carboxamide

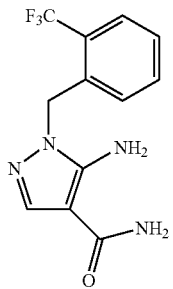 [SMILES: NC(=O)c1cnn(Cc2ccccc2C(F)(F)F)c1N]

The title compound was synthesized in analogy to Example 1 b, using 5-amino-1-[(2-trifluoromethylphenyl)methyl]-1H-pyrazole-4-carbonitrile (Example 29 a, 850 mg, 3.19 mmol) as starting material, and isolated (725 mg, 80%) as light yellow solid; MS (ESI) 285.5 [MH+].

c) 5-(2,2-Dimethyl-propionylamino)-1-[(2-trifluoromethylphenyl)methyl]-1H-pyrazole-4-carboxylic acid amide

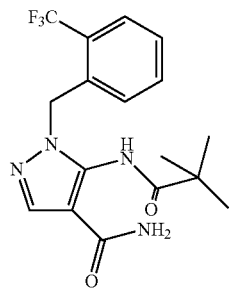 [SMILES: CC(C)(C)C(=O)Nc1c(C(N)=O)cnn1Cc1ccccc1C(F)(F)F]

The title compound was synthesized in analogy to Example 1 c, using 5-amino-1-[(2-trifluoromethylphenyl)methyl]-1H-pyrazole-4-carboxamide (Example 29 b, 720 mg, 2.53 mmol) and pivaloyl chloride (312 µL, 2.53 mmol) as starting materials, and isolated (0.95 g, quant.) as light yellow oil; MS (ESI) 396.6 [MH+].

d) 6-tert-Butyl-1,5-dihydro-1-[(2-trifluoromethylphenyl)methyl]-4H-pyrazolo[3,4-d]pyrimidin-4-one

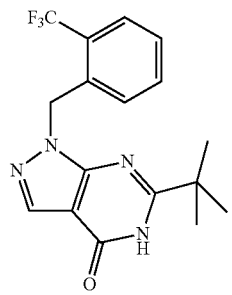 [SMILES: CC(C)(C)c1nc2c(cnn2Cc2ccccc2C(F)(F)F)c(=O)[nH]1]

The title compound was synthesized in analogy to Example 1 d, using 5-(2,2-dimethyl-propionylamino)-1-[(2-trifluoromethylphenyl)methyl]-1H-pyrazole-4-carboxylic acid amide (Example 29 c, 933 mg, 3.19 mmol) as starting material, and isolated (408 mg, 80%) as white solid; MS (ESI) 351.6 [MH+].

e) 6-tert-Butyl-4-chloro-1-[(2-trifluoromethylphenyl)methyl]-1H-pyrazolo[3,4-d]pyrimidine

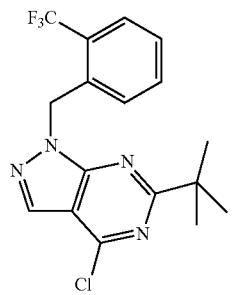 [SMILES: CC(C)(C)c1nc(Cl)c2cnn(Cc3ccccc3C(F)(F)F)c2n1]

The title compound was synthesized in analogy to Example 1 e, using 6-tert-butyl-1,5-dihydro-1-[(2-trifluoromethylphenyl)methyl]-4H-pyrazolo[3,4-d]pyrimidin-4-one (Example 29 d, 200 mg, 571 µmol) as starting material, and isolated (458 mg, quant.) as black oil that was used in the next step without further characterization.

f) (S)-1-[6-tert-Butyl-1-[(2-trifluoromethylphenyl)methyl]-1H-pyrazolo[3,4-d]pyrimidin-4-yl]-pyrrolidin-3-ol

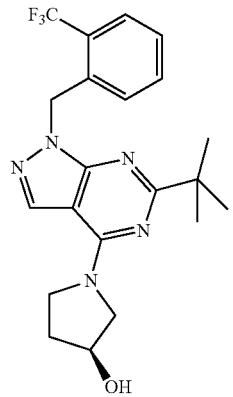 [SMILES: CC(C)(C)c1nc(N2CC[C@H](O)C2)c2cnn(Cc3ccccc3C(F)(F)F)c2n1]

The title compound was synthesized in analogy to Example 1 f, using 6-tert-butyl-4-chloro-1-[(2-trifluoromethylphenyl)methyl]-1H-pyrazolo[3,4-d]pyrimidine (Example 29 d, 211 mg, 572 µmol) and (3S)-3-pyrrolidinol (CAN 100243-39-8, 143 µL, 1.72 mmol) as starting materials, and isolated (124 mg, 42%) as white foam; LC-MS (UV peak area; ESI) 100%, 420.2022 [MH$^+$].

Example 30

(S)-1-[6-tert-Butyl-1-(2-methanesulfonyl-benzyl)-1H-pyrazolo[3,4-d]pyrimidin-4-yl]-pyrrolidin-3-ol

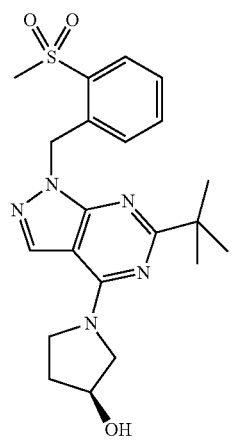 [SMILES: CC(C)(C)c1nc(N2CC[C@H](O)C2)c2cnn(Cc3ccccc3S(C)(=O)=O)c2n1]

The title compound was synthesized in analogy to Example 9, using 6-tert-butyl-4-[(S)-3-(tert-butyl-dimethyl-silanyloxy)-pyrrolidin-1-yl]-1H-pyrazolo[3,4-d]pyrimidine (Example 25 b, 30 mg, 80 µmol) and 1-(chloromethyl)-2-(methylsulfonyl)-benzene (CAN 168551-51-7; 33 mg, 160 µmol) as starting materials and isolated (2 mg, 5.8%) as colorless oil; LC-MS (UV peak area, ESI) 87.4%, 430.1911 [MH$^+$].

Example 31

(S)-1-[6-tert-Butyl-1-(1-methyl-1H-tetrazol-5-ylmethyl)-1H-pyrazolo[3,4-d]pyrimidin-4-yl]-pyrrolidin-3-ol

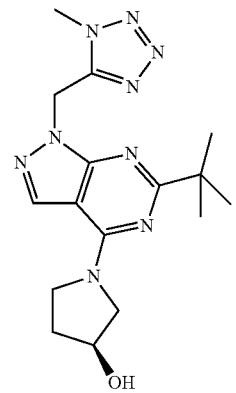 [SMILES: Cn1nnnc1Cn1ncc2c(N3CC[C@H](O)C3)nc(C(C)(C)C)nc21]

The title compound was synthesized in analogy to Example 9, using 6-tert-butyl-4-[(S)-3-(tert-butyl-dimethyl-silanyloxy)-pyrrolidin-1-yl]-1H-pyrazolo[3,4-d]pyrimidine (Example 25 b, 80 mg, 213 µmol) and 5-(chloromethyl)-1-methyl-1H-tetrazole (CAN 57235-84-4; 38 mg, 287 µmol) as starting materials and isolated (12 mg, 16%) as colorless oil; LC-MS (UV peak area, ESI) 93%, 358.7 [MH$^+$].

Example 32

(S)-1-[6-tert-Butyl-1-(3-chloro-pyridin-2-ylmethyl)-1H-pyrazolo[3,4-d]pyrimidin-4-yl]-pyrrolidin-3-ol

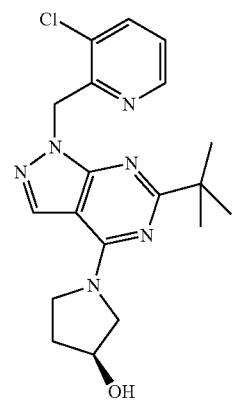

The title compound was synthesized in analogy to Example 9, using 6-tert-butyl-4-[(S)-3-(tert-butyl-dimethyl-silanyloxy)-pyrrolidin-1-yl]-1H-pyrazolo[3,4-d]pyrimidine (Example 25 b, 60 mg, 160 µmol) and 3-chloro-2-(chloromethyl)-pyridine (CAN 185315-53-1; 51.8 mg, 320 µmol) as starting materials and after an additional deprotection step with TBAF isolated (13 mg, 21%) as colorless oil; LC-MS (UV peak area, ESI) 100%, 387.1703 [MH$^+$].

Example 33

(S)-1-[6-tert-Butyl-1-(1-cyclopropyl-1H-tetrazol-5-ylmethyl)-1H-pyrazolo[3,4-d]pyrimidin-4-yl]-pyrrolidin-3-ol

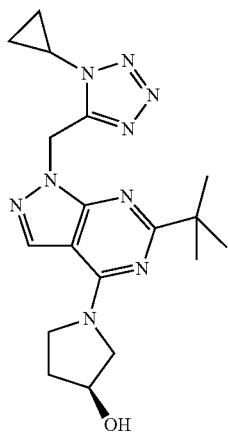 [SMILES: CC(C)(C)c1nc(N2CC[C@H](O)C2)c2cnn(Cc3nnnn3C3CC3)c2n1]

The title compound was synthesized in analogy to Example 9, using 6-tert-butyl-4-[(S)-3-(tert-butyl-dimethyl-silanyloxy)-pyrrolidin-1-yl]-1H-pyrazolo[3,4-d]pyrimidine (Example 25 b, 120 mg, 320 µmol) and 5-(chloromethyl)-1-cyclopropyl-1H-tetrazole (CAN 949980-56-7; 76 mg, 479 µmol) as starting materials and after an additional deprotection step with TBAF isolated (30 mg, 26%) as white foam; LC-MS (UV peak area, ESI) 97%, 384.7 [MH⁺].

Example 34

{(R)-1-[6-tert-Butyl-1-[(2-trifluoromethylphenyl) methyl]-1H-pyrazolo[3,4-d]pyrimidin-4-yl]pyrrolidin-2-yl}-methanol

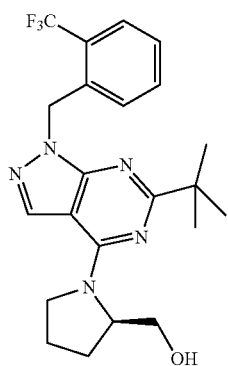 [SMILES: CC(C)(C)c1nc(N2CCC[C@@H]2CO)c2cnn(Cc3ccccc3C(F)(F)F)c2n1]

The title compound was synthesized in analogy to Example 1 f, using 6-tert-butyl-4-chloro-1-[(2-trifluoromethylphenyl)methyl]-1H-pyrazolo[3,4-d]pyrimidine (Example 29 d, 100 mg, 271 µmol) and (2R)-2-pyrrolidinemethanol (CAN 68832-13-3, 82.3 mg, 813 µmol) as starting materials, and isolated (110 mg, 94%) as colorless oil; LC-MS (UV peak area; ESI) 98%, 434.7 [MH⁺].

Example 35

6-tert-Butyl-4-((R)-2-methoxymethyl-pyrrolidin-1-yl)-1-[(2-trifluoromethylphenyl)methyl]-1H-pyrazolo[3,4-d]pyrimidine

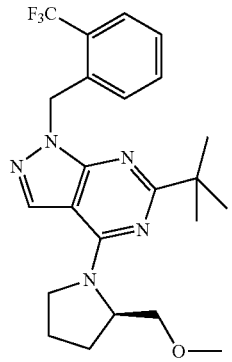 [SMILES: COC[C@H]1CCCN1c1nc(C(C)(C)C)nc2c1cnn2Cc1ccccc1C(F)(F)F]

The title compound was synthesized in analogy to Example 1 f, using 6-tert-butyl-4-chloro-1-[(2-trifluoromethylphenyl)methyl]-1H-pyrazolo[3,4-d]pyrimidine (Example 29 d, 100 mg, 271 µmol) and (2R)-2-(methoxymethyl)-pyrrolidine (CAN 84025-81-0, 93.7 mg, 813 µmol) as starting materials, and isolated (106 mg, 87%) as colorless oil; LC-MS (UV peak area; ESI) 95%, 448.7 [MH⁺].

Example 36

6-tert-Butyl-4-((R)-2-methoxymethyl-pyrrolidin-1-yl)-1-(4-methyl-furazan-3-ylmethyl)-1H-pyrazolo[3,4-d]pyrimidine a) (1,3-Dioxo-1,3-dihydro-isoindol-2-yl)-(4-methyl-furazan-3-ylmethyl)-carbamic acid tert-butyl ester

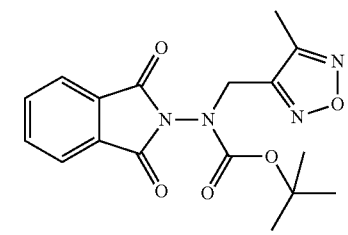 [SMILES: Cc1nonc1CN(C(=O)OC(C)(C)C)N1C(=O)c2ccccc2C1=O]

To a mixture of N-(1,3-dihydro-1,3-dioxo-2H-isoindol-2-yl)-carbamic acid 1,1-dimethylethyl ester (CAN 34387-89-8, 5.0 g, 19.1 mmol), potassium carbonate (10.5 g, 76.3 mmol) and benzyl triethylammonium chloride (0.65 g, 2.86 mmol) in acetonitrile (150 mL) was added 3-(bromomethyl)-4-methyl-1,2,5-oxadiazole (CAN 90507-32-7, 4.05 g, 22.9 mmol). The mixture was stirred at room temperature for 10 minutes, over night at 60° C. and subsequently filtered. The filtrate was concentrated in vacuo and the crude material was purified by flash chromatography (silica, ethyl acetate/heptane gradient) to afford the desired product (5.52 g, 81%) as white solid; LC-MS (UV peak area; ESI) 99%, 257.4 [M-C₄H₉CO₂⁻].

b) N-(4-Methyl-furazan-3-ylmethyl)-hydrazinecarboxylic acid tert-butyl ester

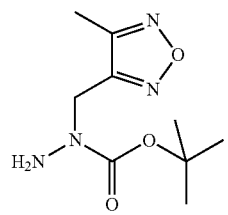 [SMILES: Cc1nonc1CN(N)C(=O)OC(C)(C)C]

To a solution of (1,3-dioxo-1,3-dihydro-isoindol-2-yl)-(4-methyl-furazan-3-ylmethyl)-carbamic acid tert-butyl ester (4.5 g, 12.6 mmol) in ethanol (50 mL) and THF (30 mL) was added hydrazine (2.0 mL, 63.7 mmol). The mixture was stirred over night at 70° C. and subsequently filtered. The filtrate was concentrated in vacuo and the crude title compound (3.0 g, quant.) was used in subsequent steps without further purification; GC-MS (TIC peak area; EI) 95%, 228 [M].

c) (4-Methyl-furazan-3-ylmethyl)-hydrazine hydrochloride (1:1)

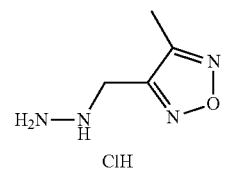

To a solution of N-(4-methyl-furazan-3-ylmethyl)-hydrazinecarboxylic acid tert-butyl ester (3.0 g, 13.1 mmol) in methanol (200 mL) was added hydrochloric acid in dioxane (4 N, 4 mL). The mixture was stirred at room temperature for 5 days at room temperature and concentrated in vacuo. The crude material was purified by recrystallization from ethyl acetate to afford the desired product in ~85% purity (2.1 g, 84%) as white solid; LC-MS (ESI) 129.0767 [MH$^+$].

d) 5-Amino-1-(4-methyl-furazan-3-ylmethyl)-1H-pyrazole-4-carbonitrile

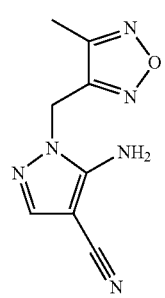

The title compound was synthesized in analogy to Example 1 a, using (4-methyl-furazan-3-ylmethyl)-hydrazine hydrochloride (1:1) (Example 26 c, 0.49 g, 2.97 mmol) and 2-(ethoxymethylene)-propanedinitrile (CAN 123-06-8, 533 mg, 3.27 mmol) as starting materials, and isolated (298 mg, 49%) as yellow solid; MS (ESI) 205.5 [MH$^+$].

e) 5-Amino-1-(4-methyl-furazan-3-ylmethyl)-1H-pyrazole-4-carboxylic acid amide

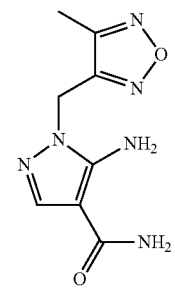 [SMILES: Cc1nonc1Cn1ncc(C(N)=O)c1N]

The title compound was synthesized in analogy to Example 1 b, using 5-amino-1-(4-methyl-furazan-3-ylmethyl)-1H-pyrazole-4-carbonitrile (Example 36 2, 298 mg, 1.47 mmol) as starting material, and isolated (310 mg, 85%) as yellow solid; MS (ESI) 223.2 [MH$^+$].

f) 5-(2,2-Dimethyl-propionylamino)-1-(4-methyl-furazan-3-ylmethyl)-1H-pyrazole-4-carboxylic acid amide

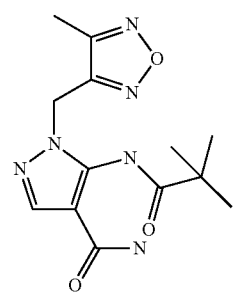 [SMILES: Cc1nonc1Cn1ncc(C(N)=O)c1NC(=O)C(C)(C)C]

The title compound was synthesized in analogy to Example 1 c, using 5-amino-1-(4-methyl-furazan-3-ylmethyl)-1H-pyrazole-4-carboxylic acid amide (Example 36 e, 360 mg, 1.62 mmol) and pivaloyl chloride (199 µL, 1.62 mmol) as starting materials, and isolated (0.49 g, quant.) as yellow oil; MS (ESI) 307.4 [MH$^+$].

g) 6-tert-Butyl-1-(4-methyl-furazan-3-ylmethyl)-1,5-dihydro-pyrazolo[3,4-d]pyrimidin-4-one

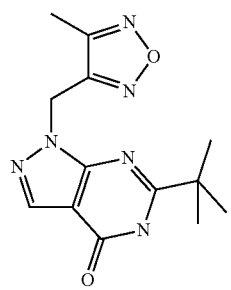 [SMILES: Cc1nonc1Cn1ncc2c(=O)[nH]c(C(C)(C)C)nc21]

The title compound was synthesized in analogy to Example 1 d, using 5-(2,2-dimethyl-propionylamino)-1-(4-methyl-furazan-3-ylmethyl)-1H-pyrazole-4-carboxylic acid amide (Example 36 f, 107 mg, 0.35 mmol) as starting material, and isolated (88 mg, 87%) as white solid; MS (ESI) 289.5 [MH⁺].

h) 6-tert-Butyl-4-chloro-1-(4-methyl-furazan-3-ylmethyl)-1H-pyrazolo[3,4-d]pyrimidine

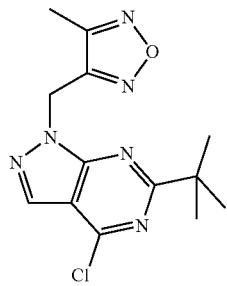 [SMILES: Cc1nonc1Cn1ncc2c(Cl)nc(C(C)(C)C)nc21]

The title compound was synthesized in analogy to Example 1 e, using 6-tert-butyl-1-(4-methyl-furazan-3-ylmethyl)-1,5-dihydro-pyrazolo[3,4-c]pyrimidin-4-one (Example 36 g, 135 mg, 468 μmol) as starting material, and isolated (144 mg, quant.) as yellow oil that was used in the next step without further characterization.

i) 6-tert-Butyl-4-((R)-2-methoxymethyl-pyrrolidin-1-yl)-1-(4-methyl-furazan-3-ylmethyl)-1H-pyrazolo[3,4-c]pyrimidine

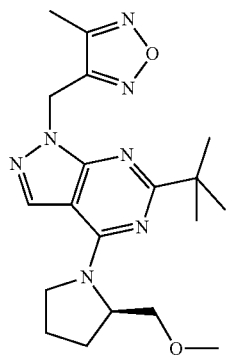 [SMILES: COC[C@H]1CCCN1c1nc(C(C)(C)C)nc2c1cnn2Cc1nonc1C]

The title compound was synthesized in analogy to Example 1 f, using 6-tert-butyl-4-chloro-1-(4-methyl-furazan-3-ylmethyl)-1H-pyrazolo[3,4-c]pyrimidine (Example 36 h, 144 mg, 468 μmol) and (2R)-2-(methoxymethyl)-pyrrolidine (CAN 84025-81-0, 93.3 mg, 810 μmol) as starting materials, and isolated (125 mg, 69%) as brown oil; LC-MS (UV peak area; ESI) 98.5%, 386.2311 [MH⁺].

Example 37

6-Chloro-4-(3,3-difluoropyrrolidin-1-yl)-1-[[2-(trifluoromethyl)phenyl]methyl]pyrazolo[3,4-d]pyrimidine a) 4,6-Dichloro-1-(2-(trifluoromethyl)benzyl)-1H-pyrazolo[3,4-d]pyrimidine

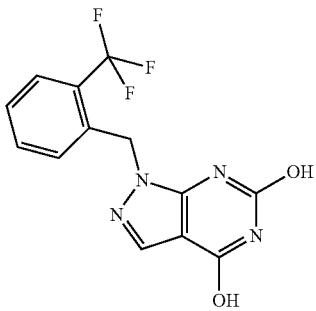 [SMILES: Oc1nc(O)c2cnn(Cc3ccccc3C(F)(F)F)c2n1]

A suspension of 5-amino-1-[(2-trifluoromethylphenyl)methyl]-1H-pyrazole-4-carboxamide (2500 mg, 8.8 mmol, Example 29 b), diethyl carbonate (1.25 g, 1.28 mL, 10.6 mmol) and sodium tert-butoxide (1.69 g, 17.6 mmol) in ethanol (70 mL) and DMSO (10 mL) was stirred for 8 d at 100° C. The yellow suspension was cooled to 0° C. and filtrated. The residue washed with tBuOMe and the combined filtrates were concentrated in vacuo. Heptane was added to precipitate the title compound (2.4 g, 84%) as white solid which was used in the next step without further purification; MS (ESI) 311.5 [MH⁺].

b) 4,6-Dichloro-1-(2-(trifluoromethyl)benzyl)-1H-pyrazolo[3,4-d]pyrimidine

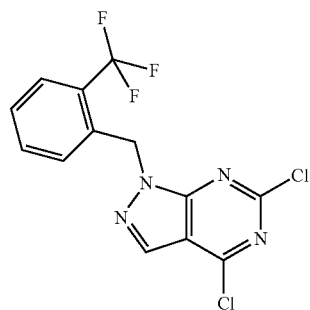 [SMILES: FC(F)(F)c1ccccc1Cn1ncc2c(Cl)nc(Cl)nc21]

A mixture of 1-(2-(trifluoromethyl)benzyl)-1H-pyrazolo[3,4-d]pyrimidine-4,6-diol (500 mg, 1.61 mmol) and POCl₃ (12.4 g, 7.51 mL, 80.6 mmol) and N,N-diethylaniline (433 mg, 464 μL, 2.9 mmol) was heated under stirring for 2 h to 110° C. The crude reaction mixture was concentrated in vacuo, poured into 25 mL dichloromethane and washed with ice water (2×25 mL). The combined aqueous layers were back-extracted with dichloromethane (1×25 mL). The combined organic layers were dried over MgSO₄ and concentrated in vacuo. The crude material was purified by chromatography (silica gel, 20 g, AcOEt/heptane 1/3) to give the title compound (50 mg, 9%) as white solid; MS (ESI) 347.4 [MH⁺].

c) 6-Chloro-4-(3,3-difluoropyrrolidin-1-yl)-1-[[2-(trifluoromethyl)phenyl]methyl]pyrazolo[3,4-d]pyrimidine

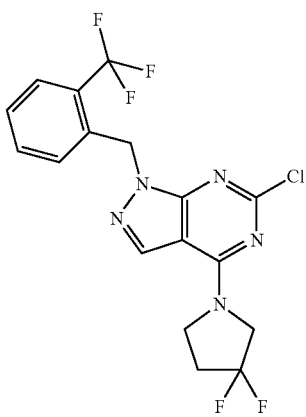 [SMILES: FC1(F)CCN(c2nc(Cl)nc3c2cnn3Cc2ccccc2C(F)(F)F)C1]

A mixture of 4,6-dichloro-1-(2-(trifluoromethyl)benzyl)-1H-pyrazolo[3,4-d]pyrimidine (50 mg, 144 μmol), 3,3-difluoropyrrolidine hydrochloride (32 mg, 223 μmol) and DIPEA (74 mg, 100 μL, 573 μmol) in dioxane (2 mL) was heated in a microwave oven to 120° C. for 30 min. The solvent was removed under reduce pressure and the crude material was purified by chromatography (silica gel, 20 g, AcOEt/heptane 1/3). Recrystallization from EtOAc and heptane afforded the title compound (35 mg, 58%) as white solid; LC-MS (UV peak area; ESI) 99%, 418.0865 [MH+].

Example 38

4-(3,3-Difluoropyrrolidin-1-yl)-6-(2,2-dimethylpropoxy)-1-[[2-(trifluoromethyl)phenyl]methyl]pyrazolo[3,4-d]pyrimidine

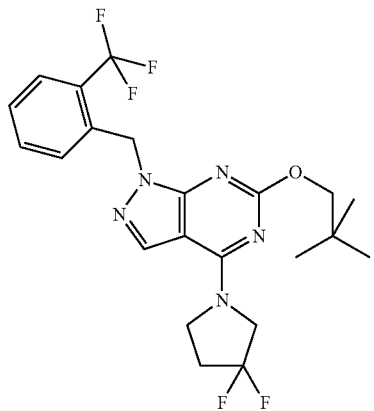 [SMILES: CC(C)(C)COc1nc(N2CCC(F)(F)C2)c2cnn(Cc3ccccc3C(F)(F)F)c2n1]

Sodium hydride (6.61 mg, 165 μmol) and 2,2-dimethyl-1-propanol (48.5 mg, 59.3 μL, 551 μmol) were added to a solution of 6-chloro-4-(3,3-difluoropyrrolidin-1-yl)-1-(2-(trifluoromethyl)benzyl)-1H-pyrazolo[3,4-d]pyrimidine (46 mg, 110 μmol; Example 37 c) in THF (1 mL). The reaction mixture was stirred for 4 h at 80° C., poured into 25 mL EtOAc and washed with water (2×20 mL). The combined aqueous layers were back-extracted with EtOAc (1×25 mL). The combined organic layers were dried over MgSO4 and concentrated in vacuo. The crude material was purified by flash chromatography (silica gel, 20 g, 0% to 50% EtOAc in heptane) to give the title compound (35 mg, 68%) as white solid; MS (ESI) 470.7 [MH+].

Example 39

Pharmacological Tests

The following tests were carried out in order to determine the activity of the compounds of formula (I):
Radioligand Binding Assay The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl$_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.
cAMP Assay CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1x HT supplement, with 10% fetal calf serum and incubated at 5% CO$_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% NaN$_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

EC$_{50}$ values were determined using Activity Base analysis (ID Business Solution, Limited). The EC$_{50}$ values for a wide range of cannabinoid agonists generated from this assay were in agreement with the values published in the scientific literature.

The compounds of the invention are CB2 receptor agonists with $EC_{50}$ below 1 µM and selectivity versus CB1 in the corresponding assay of at least 10 fold. Particular compound of the invention are CB2 receptor agonists with $EC_{50}$ below 0.01 µM and selectivity versus CB1 in the corresponding assay of at least 2000 fold.

For example, the following compounds showed the following human $EC_{50}$ values in the functional cAMP assay described above:

| Example | human CB2 $EC_{50}$ [µM] | human CB1 $EC_{50}$ [µM] |
| --- | --- | --- |
| 1 | 0.0048 | >10 |
| 2 | 0.0033 | >10 |
| 3 | 0.0051 | >10 |
| 4 | 0.0042 | >10 |
| 5 | 0.0255 | >10 |
| 6 | 0.0059 | >10 |
| 7 | 0.0011 | >10 |
| 8 | 0.0054 | >10 |
| 9 | 0.0005 | >10 |
| 10 | 0.0007 | 0.3368 |
| 11 | 0.0187 | >10 |
| 12 | 0.0016 | 1.5741 |
| 13 | 0.0196 | >10 |
| 14 | 0.0013 | >10 |
| 15 | 0.0009 | >10 |
| 16 | 0.0006 | >10 |
| 17 | 0.003 | >10 |
| 18 | 0.0262 | >10 |
| 19 | 0.0014 | >10 |
| 20 | 0.0016 | >10 |
| 21 | 0.0034 | >10 |
| 22 | 0.0084 | >10 |
| 23 | 0.0055 | >10 |
| 24 | 0.0175 | >10 |
| 25 | 0.0004 | >10 |
| 26 | 0.0356 | >10 |
| 27 | 0.0425 | >10 |
| 28 | 0.0019 | >10 |
| 29 | 0.0019 | >10 |
| 30 | 0.0024 | >10 |
| 31 | 0.0173 | >10 |
| 32 | 0.0015 | >10 |
| 33 | 0.0088 | >10 |
| 34 | 0.005 | >10 |
| 35 | 0.0133 | >10 |
| 36 | 0.0014 | >10 |
| 37 | 0.0172 | >10 |
| 38 | 0.0160 | >10 |

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

| Ingredients | Per tablet | |
| --- | --- | --- |
| Film Coat: | | |
| Hydroxypropyl methyl cellulose | 3.5 mg | 7.0 mg |
| Polyethylene glycol 6000 | 0.8 mg | 1.6 mg |
| Talc | 1.5 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate coverage and sterilized.

The invention claimed is:
1. A compound of formula (I)

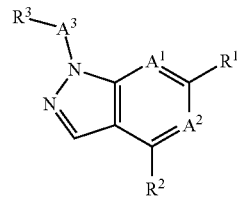

wherein
$A^1$ is CH or N;
$A^2$ is CH or N;
$A^3$ is —$(CH_2)_n$— or —$CH_2C(O)$—;

R¹ is alkyl, cycloalkyl, alkoxy or halogen;
R² is substituted pyrrolidinyl or substituted dihydropyrrolyl, wherein substituted pyrrolidinyl and substituted dihydropyrrolyl are pyrrolidinyl and dihydropyrrolyl substituted with one or two substituents independently selected from halogen, hydroxyl, hydroxyalkyl, alkoxyalkyl and alkylfurazanylalkoxy;
R³ is phenyl, substituted phenyl, substituted furazanyl, pyridinyl, substituted pyridinyl, dioxothietanyl, tetrahydrofuranyl, substituted tetrazolyl or substituted triazolyl, wherein substituted phenyl, substituted furazanyl, substituted pyridinyl and substituted triazolyl are phenyl, pyridinyl and triazolyl substituted with one or two substituents independently selected from alkyl, alkoxy, halogen, haloalkyl, alkylsulfonyl and cycloalkyl, and wherein substituted tetrazolyl and substituted furazanyl are tetrazolyl and furazanyl substituted with one substituent selected from alkyl, alkoxy, halogen, haloalkyl, alkylsulfonyl and cycloalkyl;
n is 0, 1 or 2;
provided that A¹ and A² are not both CH at the same time;
or a pharmaceutically acceptable salt or ester thereof.

2. A compound according to claim 1, wherein A¹ is N.
3. A compound according to claim 1, wherein A² is N.
4. A compound according to claim 1, wherein A³ is —(CH₂)ₙ—.
5. A compound according to claim 1, wherein R¹ is alkyl.
6. A compound according to claim 1, wherein R¹ is tert.-butyl.
7. A compound according to claim 1, wherein R² is substituted pyrrolidinyl, wherein substituted pyrrolidinyl is pyrrolidinyl substituted with one or two substituents independently selected from halogen and hydroxyl.
8. A compound according to claim 1, wherein R² is difluoropyrrolidinyl or hydroxypyrrolidinyl.
9. A compound according to claim 1, wherein R³ is substituted phenyl, substituted furazanyl, substituted pyridinyl, substituted tetrazolyl or substituted triazolyl, wherein substituted phenyl, substituted pyridinyl and substituted triazolyl are phenyl, pyridinyl and triazolyl substituted with one or two substituents independently selected from alkyl, halogen and haloalkyl, wherein substituted tetrazolyl is tetrazolyl substituted with one substituent selected from alkyl, and cycloalkyl, and wherein substituted furazanyl is furazanyl substituted with alkyl.
10. A compound according to claim 1, wherein R³ is trifluoromethylphenyl, methylfurazanyl, chloropyridinyl, methyltetrazolyl, cyclopropyltetrazolyl, dimethyltriazolyl or methyltriazolyl.
11. A compound according to claim 1, wherein n is 1.
12. A compound selected from the group consisting of:
6-tert-Butyl-4-(3,3-difluoro-pyrrolidin-l-yl)-[(4-methoxyphenyl)methyl]-1H-pyrazolo [3,4-d]pyrimidine;
1-Benzyl-6-tert-butyl-4-(3,3-difluoro-pyrrolidin-1-yl)-1H-pyrazolo[3,4-d ]pyrimidine;
(S)-1-[6-tert-Butyl-1-[(2-chlorophenyl)methyl]-1H-pyrazolo[3,4-d]pyrimidin-4-yl]-pyrrolidin-3-ol;
6-tert-Butyl-1-[(2-chlorophenyl)methyl]-4-(3,3-difluoro-pyrrolidin-1-yl)-1H-pyrazolo [3,4-d]pyrimidine;
6-tert-Butyl-1-[(2-chlorophenyl)methyl]-4-ethoxy-1H-pyrazolo[3,4-d]pyrimidine;
6-tert-Butyl- 1-[(2-chloro-4-fluorophenyl)methyl ]-4-(3 ,3-difluoro-pyrrolidin-1-yl)-1H-pyrazolo[3,4-d]pyrimidine;
6-tert-Butyl-4-(3,3-difluoro-pyrrolidin-1-yl)-1-[(2-trifluoromethylphenyl)methyl]-1H-pyrazolo[3,4-d]pyrimidine;
6-tert-Butyl-4-(3,3-difluoro-pyrrolidin-1-yl)-1-phenethyl-1H-pyrazolo[3,4-d]pyrimidine;
6-tert-Butyl-4-(3,3-difluoro-pyrrolidin-1-yl)-1-(4-methyl-furazan-3-ylmethyl)-1H-pyrazolo [3,4-d]pyrimidine;
6-tert-Butyl-4-(3,3-difluoro-pyrrolidin-1-yl)-1-(2-methanesulfonyl-benzyl)-1H-pyrazolo [3,4-d]pyrimidine;
6-tert-Butyl-4-(3,3-difluoro-pyrrolidin-1-yl)-1-(2-pyridin-3-yl-ethyl)-1H-pyrazolo [3,4-d]pyrimidine;
6-tert-Butyl-1-(2-chloro-pyridin-3-ylmethyl)-4-(3,3-difluoro-pyrrolidin-1-yl)-1H-pyrazolo [3,4-d]pyrimidine;
6-tert-Butyl-4-(3,3-difluoro-pyrrolidin- 1-yl)- 1-(1,1-dioxo-1λ6-thietan-3-yl)-1H-pyrazolo [3,4-d]pyrimidine;
6-tert-Butyl-4-(3,3-difluoro-pyrrolidin-1-yl)-1-(tetrahydro-furan-3-yl)-1H-pyrazolo [3,4-d]pyrimidine;
6-tert-Butyl-4-(3,3-difluoro-pyrrolidin- 1-yl)-1-(1-methyl- 1H-tetrazol-5-ylmethyl)-1H-pyrazolo[3,4-d]pyrimidine;
6-tert-Butyl -1-(1-cyclopropyl- 1H-tetrazol-5-ylmethyl)-4-(3,3-difluoro-pyrrolidin- 1-yl)-1H-pyrazolo[3,4-d]pyrimidine;
6-tert-Butyl-4-(3,3-difluoro-pyrrolidin- 1-yl)- 1-(4,5-dimethyl-4H-[1,2,4]triazol-3-ylmethyl)-1H-pyrazolo[3,4-d]pyrimidine;
6-tert-Butyl- 1-(4,5-dimethyl-4H-[1,2,4]triazol-3-ylmethyl)-4-(3-fluoro-2,5-dihydro-pyrrol-1-yl)-1H-pyrazolo[3,4-d]pyrimidine;
6-tert-Butyl-4-(3,3-difluoro-pyrrolidin- 1-yl)- 1-(3-methyl-3H-[1,2,3 ]triazol-4-ylmethyl)-1H-pyrazolo[3, 4-d]pyrimidine;
6-tert-Butyl-4-(3-fluoro-2,5-dihydro-pyrrol- 1-yl)- 1-(3-methyl-3H-[1,2,3 ]triazol-4-ylmethyl)-1H-pyrazolo[3, 4-d]pyrimidine;
2-[6-tert-Butyl-4-(3,3-difluoro-pyrrolidin-1-yl)-pyrazolo [3,4-d]pyrimidin-1-yl]-1-pyridine-4-yl-ethanone;
2-[6-tert-Butyl-4-(3,3-difluoro-pyrrolidin-1-yl)-pyrazolo [3,4-d]pyrimidin-1-yl]-1-pyridine-2-yl-ethanone;
(S)-1-[6-tert-Butyl-1-[(4-methoxyphenyl)methyl ]-1H-pyrazolo[3,4-d]pyrimidin-4-yl]-pyrrolidin-3-ol;
6-Cyclopropyl-4-(3,3-difluoro-pyrrolidin- 1-yl)-1-[(4-methoxyphenyl)methyl]-1H-pyrazolo [3,4-b]pyrimidine;
(S)- 1-[6-tert-Butyl-1-(4-methyl-furazan-3-ylmethyl)-1H-pyrazolo[3,4-d]pyrimidin-4-yl]-pyrrolidin-3-ol;
6-tert-Butyl-4-[(S)-3-(4-methyl-furazan-3-ylmethoxy)-pyrrolidin- 1-yl]-1-(4-methyl-furazan-3-ylmethyl)-1H-pyrazolo[3,4-d]pyrimidine;
6-Cyclopropyl-4-(3,3-difluoro-pyrrolidin- 1-yl)- 1-(4-methyl-furazan-3-ylmethyl)-1H-pyrazolo[4,3-c]pyridine;
6-Cyclopropyl-4-(3,3-difluoro-pyrrolidin- 1-yl)-1-(4-methyl-furazan-3-ylmethyl)-1H-pyrazolo[3,4-b]pyridine;
(S)-1-[6-tert-Butyl -1-[(2-trifluoromethylphenyl)methyl]-1H-pyrazolo[3,4-d]pyrimidin-4-yl]-pyrrolidin-3-ol;
(S)-1-[6-tert-Butyl-1-(2-methanesulfonyl-benzyl)-1H-pyrazolo [3,4-d]pyrimidin-4-yl]-pyrrolidin-3-ol;
(S)-1-[6-tert-Butyl- 1-(1-methyl- 1H-tetrazol-5-yl methyl)-1H-pyrazolo[3,4-d]pyrimidin-4-yl]-pyrrolidin-3-ol;
(S)-1-[6-tert-Butyl-1-(3-chloro-pyridin-2-ylmethyl)-1H-pyrazolo[3,4-d]pyrimidin-4-yl]-pyrrolidin-3-ol;
(S)-1-[6-tert-Butyl-1-(1-cyclopropyl- 1H-tetrazol-5-ylmethyl)-1H-pyrazolo[3,4-d]pyrimidin-4-yl]-pyrrolidin-3-ol;
{(R)-1-[6-tert-Butyl-1-[(2-trifluoromethylphenyl) methyl]- 1H-pyrazolo[3,4-d]pyrimidin-4-yl]-pyrrolidin-2-yl}-methanol;

6-tert-Butyl-4-((R)-2-methoxymethyl-pyrrolidin-1-yl)-1-[(2-trifluoromethylphenyl)methyl]-1H-pyrazolo[3,4-d]pyrimidine;

6-tert-Butyl-4-((R)-2-methoxymethyl-pyrrolidin-1-yl)-1-(4-methyl-furazan-3-ylmethyl)-1H-pyrazolo[3,4-d]pyrimidine;

6-Chloro-4-(3,3-difluoropyrrolidin-1-yl)-1-[[2-(trifluoromethyl)phenyl]methyl]pyrazolo[3,4-d]pyrimidine ; and 4-(3,3-Difluoropyrrolidin-1-yl)-6-(2,2-dimethylpropoxy)- 1 -[[2-(trifluoromethyl)phenyl]methyl]pyrazolo[3,4-d]pyrimidine.

13. A compound according to claim 1 selected from the group consisting of:

6-tert-Butyl-4-(3,3-difluoro-pyrrolidin-1-yl)-1-[(2-trifluoromethylphenyl)methyl]-1H-pyrazolo[3,4-d]pyrimidine;

6-tert-Butyl-4-(3,3-difluoro-pyrrolidin-1-yl)-1-(4-methyl-furazan-3-ylmethyl)-1H-pyrazolo[3,4-d]pyrimidine;

6-tert-Butyl- 1-(2-chloro-pyridin-3-ylmethyl)-4-(3,3-difluoro-pyrrolidin-1-yl)-1H-pyrazolo[3,4-d]pyrimidine;

6-tert-Butyl-4-(3,3-difluoro-pyrrolidin-1-yl)-1-(1-methyl-1H-tetrazol-5-ylmethyl)-1 H-pyrazolo[3,4-d]pyrimidine;

6-tert-Butyl-1-(1-cyclopropyl-1H-tetrazol-5-ylmethyl)-4-(3,3-difluoro-pyrrolidin-1-yl)-1H-pyrazolo[3,4-d]pyrimidine;

6-tert-Butyl-4-(3,3-difluoro-pyrrolidin-1-yl)-1-(4,5-dimethyl-4H-[1,2,4]triazol-3-ylmethyl)-1H-pyrazolo[3,4-d]pyrimidine;

6-tert-Butyl-4-(3,3-difluoro-pyrrolidin-1-yl)-1-(3-methyl-3H-[1,2,3]triazol-4-ylmethyl)-1H-pyrazolo[3,4-d]pyrimidine;

(S)-1-[6-tert-Butyl-1-(4-methyl-furazan-3-ylmethyl)-1H-pyrazolo[3,4-d]pyrimidin-4-yl]-pyrrolidin-3-ol; and (S)-1-[6-tert-Butyl-1-[(2-trifluoromethylphenyl)methyl]-1H-pyrazolo[3,4-d]pyrimidin-4-yl]-pyrrolidin-3-ol.

14. A process for the preparation of a compound according to claim 1, comprising one of the following steps:

(a) the reaction of a compound of formula (A)

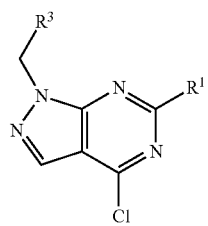

in the presence of $R^2H$ and a base;

(b) the reaction of a compound of formula (B)

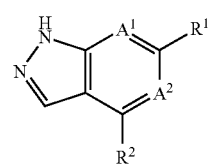

in the presence of $R^3$-$A^3$-X and a base;

(c) the reaction of a compound of formula (C)

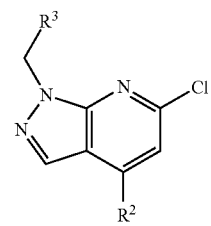

in the presence of $MR^1$, a palladium catalyst and a base; or (d) the reaction of a compound of formula (D)

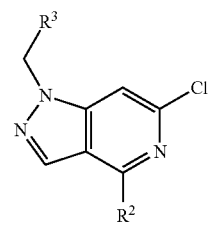

in the presence of $MR^1$, a palladium catalyst and a base;

wherein $A^1$ to $A^3$ and $R^1$ to $R^3$ are as defined in claim 1, X is a leaving group and M is a suitably substituted metal species.

15. A compound manufactured according to a process of claim 14.

16. A pharmaceutical composition comprising a compound in accordance with claim 1 and a therapeutically inert carrier.

* * * * *